United States Patent
Šiurkus et al.

(10) Patent No.: US 10,196,666 B2
(45) Date of Patent: *Feb. 5, 2019

(54) PROTEIN PRODUCTION

(71) Applicants: Juozas Šiurkus, Kaisiadorys (LT); Peter Neubauer, Berlin (DE)

(72) Inventors: Juozas Šiurkus, Kaisiadorys (LT); Peter Neubauer, Berlin (DE)

(73) Assignee: THERMO FISHER SCIENTIFIC BALTICS UAB, Vilnius (LT)

( * ) Notice: Subject to any disclaimer, the term of this patent is extended or adjusted under 35 U.S.C. 154(b) by 50 days.

This patent is subject to a terminal disclaimer.

(21) Appl. No.: 15/200,079

(22) Filed: Jul. 1, 2016

(65) Prior Publication Data

US 2017/0029861 A1 Feb. 2, 2017

Related U.S. Application Data

(63) Continuation of application No. 13/354,748, filed on Jan. 20, 2012, now Pat. No. 9,410,177.

(30) Foreign Application Priority Data

Feb. 2, 2011 (GB) .................................. 01101794.4

(51) Int. Cl.
C12P 21/02 (2006.01)
C12N 1/20 (2006.01)

(52) U.S. Cl.
CPC ............... *C12P 21/02* (2013.01); *C12N 1/20* (2013.01)

(58) Field of Classification Search
None
See application file for complete search history.

(56) References Cited

U.S. PATENT DOCUMENTS

| | | | | |
|---|---|---|---|---|
| 4,572,798 A | * | 2/1986 | Koths | C07K 1/1133 424/85.2 |
| 6,333,175 B1 | | 12/2001 | Glockshuber et al. | |
| 7,560,248 B1 | | 6/2009 | Raines | |
| 2004/0219529 A1 | | 11/2004 | Latham et al. | |
| 2005/0064545 A1 | | 3/2005 | DeMarco et al. | |
| 2010/0021964 A1 | | 1/2010 | Bornscheuer et al. | |

FOREIGN PATENT DOCUMENTS

| | | | |
|---|---|---|---|
| EP | 0422217 | * 1/1990 | ............... C12P 21/00 |
| WO | 90/03430 | 4/1990 | |
| WO | 90/12881 | 11/1990 | |
| WO | 95/30428 | 11/1995 | |
| WO | 06/014899 | 2/2006 | |
| WO | 06/091892 | 8/2006 | |

OTHER PUBLICATIONS

Chen et al., Biological functions of the disulfides in bovine pancreatic deoxyribonuclease, Protein Science (2004), 13:875-883.*
Leland et al., Ribonuclease A variants with potent cytotoxic activity, Proc. Natl. Acad. Sci. USA 95 (1998).*
Search Report issued by the UK Patents Directorate regarding App. No. GB1101794.4, dated Jun. 2, 2011.
Baneyx and Mujacic, Recombinant protein folding and misfolding in *Escherichia coli*. Nat Biotechnol. vol. 22, No. 11 (2004), pp. 1399-1408.
Blackburn et al., Ribonuclease inhibitor from human placenta: Purification and properties. J Biol Chem., vol. 252, No. 16 (1977), pp. 5904-5910.
Blackburn, Ribonuclease inhibitor from human placenta: rapid purification and assay. J Biol Chem., vol. 254, No. 24 (1979), pp. 12484-12487.
Braakman et al., Manipulating disulfide bond formation and protein folding in the endoplasmic reticulum. EMBO J., vol. 11, No. 5 (1992), pp. 1717-1722.
De Marco, Strategies for successful recombinant expression of disulfide bond-dependent proteins in *Escherichia coli*. . . Microb Cell Fact. May 14, 2009;8:26, available at http://www.microbialcellfactories.com/content/8/1/26.
Dickson et al., Ribonuclease inhibitor: structure and function. Prog Nucleic Acid Res Mol Biol, vol. 80 (2005), pp. 349-374.
Espesset et al., The channel domain of colicin A is inhibited by its immunity protein through direct interaction in the *Escherichia coli* inner membrane. EMBO J., vol. 15, No. 10 (1996), pp. 2356-2364, available at http://www.ncbi.nlm.nih.gov/pmc/articles/PMC450165/pdf/emboj00010-0036.pdf.
Fahnert, Folding-promoting agents in recombinant protein production. Methods in Molecular Biology, vol. 267 (2004) pp. 53-74.
Fominaya and Hofsteenge, Inactivation of ribonuclease inhibitor by thiol-disulfide exchange. J Biol Chem, vol. 267, No. 34 (1992), 24655-24660.
Francis and Page, Strategies to optimize protein expression in *E. coli*. Curr Protoc Protein Sci. Aug. 2010;Chapter 5:Unit 5. 24. 1-29.
Garive et al., The growth of *Escherichia coli* in buffer substrate and distilled water. J. Bacteriol, pp. 393-398, vol. 69(4) (Apr. 1955).
Gill et al., Generating controlled reducing environments in aerobic recombinant *Escherichia coli* fermentations: effects on cell growth, oxygen uptake, heat shock protein expression, and in vivo CAT activity. Biotechnology and Bioengineering, vol. 59, No. 2 (1998), pp. 248-259.
Jämsä et al., Selective retention of secretory proteins in the yeast endoplasmic reticulum by treatment of cells with a reducing agent. Yeast. vol. 10 (1994), pp. 355-370.

(Continued)

*Primary Examiner* — Nancy A Treptow
(74) *Attorney, Agent, or Firm* — Thompson Hine LLP

(57) ABSTRACT

A method for producing from host cells a heterologous polypeptide or protein comprising at least one cysteine residue in a reduced state. The method cultured the host cells in a culture medium comprising a reducing agent; and recovered the heterologous polypeptide or protein comprising at least one cysteine residue in a reduced state from the host cells or from the culture medium, where the host cells comprise a nucleic acid encoding the heterologous protein or polypeptide, and where the reducing agent is capable of permeating the plasma membrane of the host cells.

19 Claims, 19 Drawing Sheets

(56) References Cited

OTHER PUBLICATIONS

Klink et al., High-level soluble production and characterization of porcine ribonuclease inhibitor. Protein Expr Purif, vol. 22 (2001), pp. 174-179.

Kobe and Kajava, The leucine-rich repeat as a protein recognition motif. Curr Opin Struct Biol vol. 11 (2001), pp. 725-732.

Kraft et al., A dual expression platform to optimize the soluble production of heterologous proteins in the periplasm of *Escherichia coli*. Appl Microbiol Biotechnol vol. 76 (2007), pp. 1413-1422.

Lee and Vallee, Expression of human placental ribonuclease inhibitor in *Escherichia coli*. Biochem Biophys Res Commun, vol. 160, No. 1 (1989), 115-120.

Mezghrani et al., Manipulation of oxidative protein folding and PDI redox state in mammalian cells. EMBO J. vol. 20, No. 22 (2001), pp. 6288-6296.

Nishinara et al., Chaperone Coexpression Plasmids: Differential and Synergistic Roles of DnaK-DnaJ-GrpE and GroEL-GroES in Assisting Folding of an Allergen of Japanese Cedar Pollen, Cryj2, in *Escherichia coli*. Applied and Environmenatl Microbiology; 64(5):1694-9 (May 1998).

Ostermeier et al., Eukaryotic protein disulfide isomerase complements *Escherichia coli* dsbA mutants and increases the yield of a heterologous secreted protein with disulfide bonds. J Biol Chem, vol. 271, No. 18 (1996), pp. 10616-10622.

Park et al., Lrrce: a leucine-rich repeat cysteine capping motif unique to the chordate lineage. BMC Genomics 2008, 9: 599, available at http://www.biomedcentral.com/1471-2164/9/599.

Paunola et al., Folding of active beta-lactamase in the yeast cytoplasm before translocation into the endoplasmic reticulum. Mol Biol Cell., vol. 9 (1998), pp. 817-827.

Peterson et al., Bacterial Cell Surface Damage Due to Centrifugal Compaction. Applied and Environmental Mictobiology. vol. 78, No. 1, pp. 120-125 (Jan. 2012).

Schäffner et al., Cosecretion of chaperones and low-molecular-size medium additives increases the yield of recombinant disulfide-bridged proteins. Appl Environ Microbiol, vol. 67, No. 9 (2001), pp. 3994-4000.

Šiurkus et al., Novel approach of high cell density recombinant bioprocess development: Optimisation and scale-up from microlitre to pilot scales while maintaining the fed-batch cultivation mode of *E. coli* cultures. Article No. 35. Microbial Cell Factories 9 (2010) available at http://www.microbialcellfactories.com/content/pdf/1475-2859-9-35.pdf.

Valetti and Sitia, The differential effects of dithiothreitol and 2-mercaptoethanol on the secretion of partially and completely assembled immunoglobulins suggest that thiol-mediated retention does not take place in or beyond the Golgi, Mol Biol Cell, vol. 5 (1994), pp. 1311-1324.

Vicentini et al., Protein chemical and kinetic characterization of recombinant porcine ribonuclease inhibitor expressed in *Saccharomyces cerevisiae*. Biochemistry, vol. 29 (1990), pp. 8827-8834.

Walker and Gilbert, Effect of redox environment on the in vitro and in vivo folding of RTEM-1 beta-lactamase and *Escherichia coli* alkaline phosphatase. J Biol Chem vol. 269, No. 45 (1994), pp. 28487-28493.

Wunderlich and Glockshuber, In vivo control of redox potential during protein folding catalyzed by bacterial protein disulfide-isomerase (DsbA). J Biol Chem., vol. 268, No. 33 (1993), pp. 24547-24550.

Yoon et al., Influence of reducing agents on the secretion rate of recombinant erythropoietin from CHO cells. Biotechnology Letters, vol. 20 (1998), pp. 101-104.

* cited by examiner

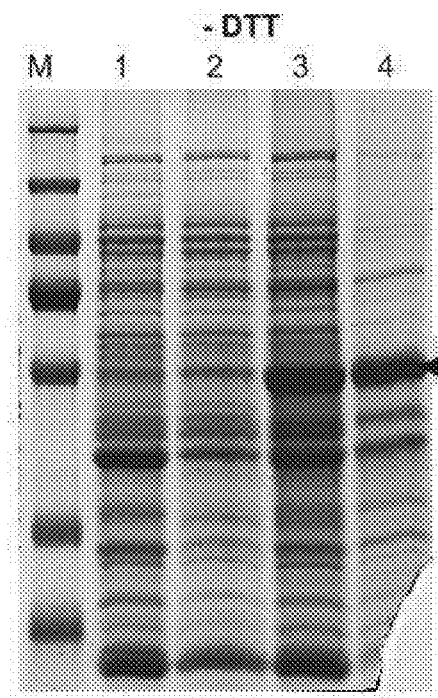
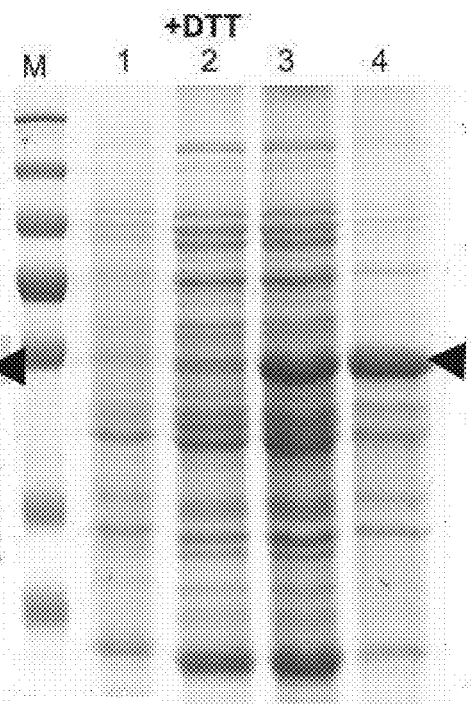
FIG. 6A        FIG. 6B
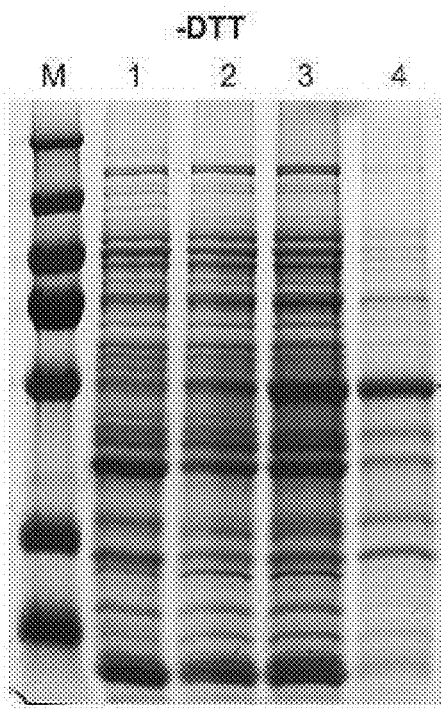
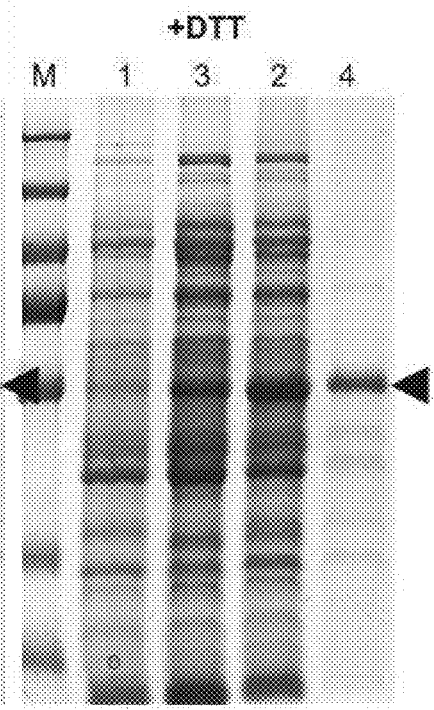
FIG. 6C        FIG. 6D

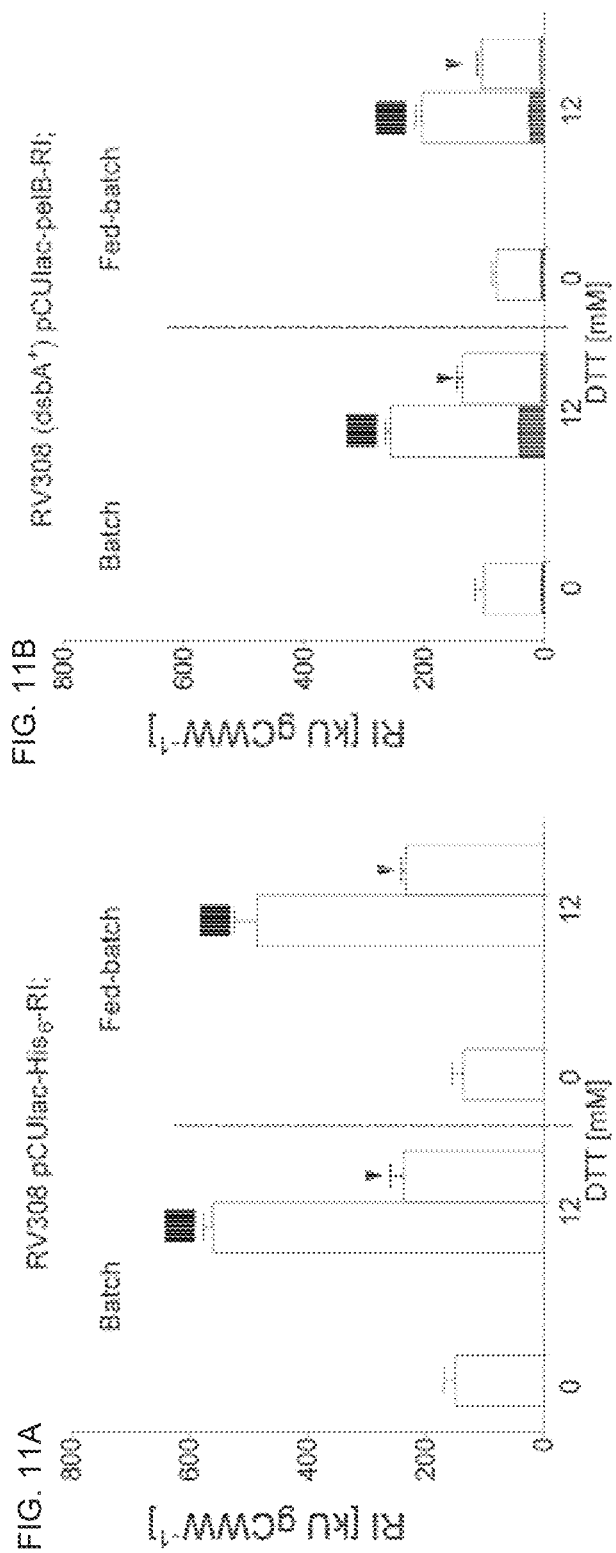

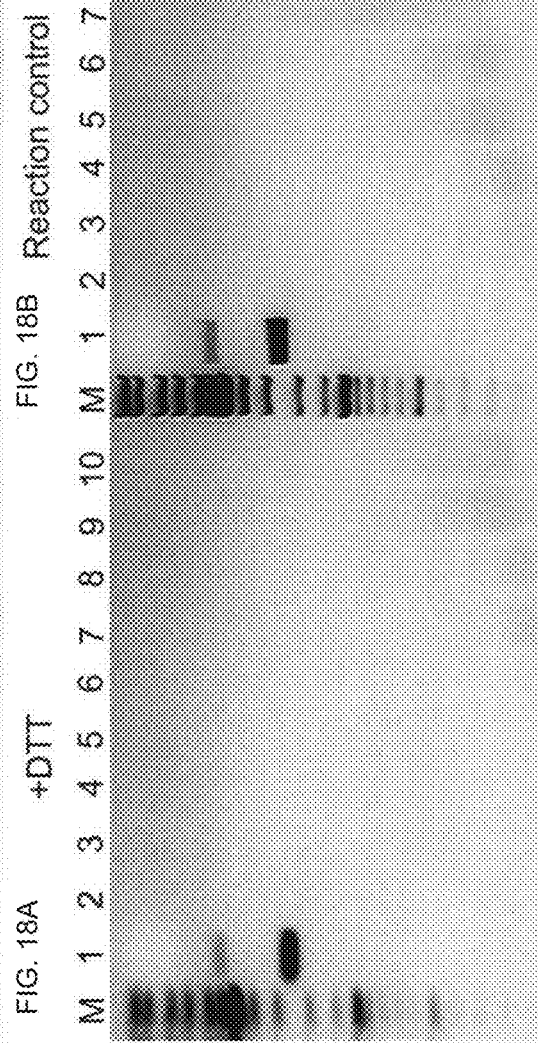
FIG. 18A  FIG. 18B  FIG. 18C  FIG. 18D

FIG. 19
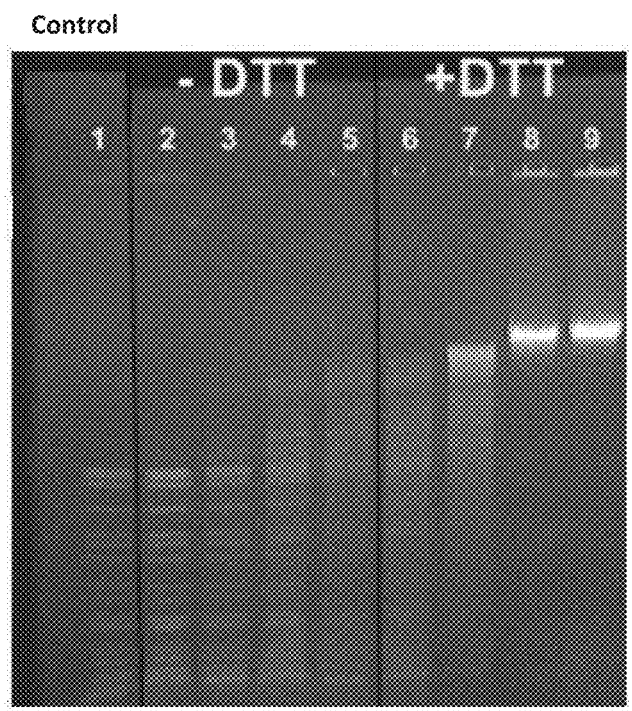
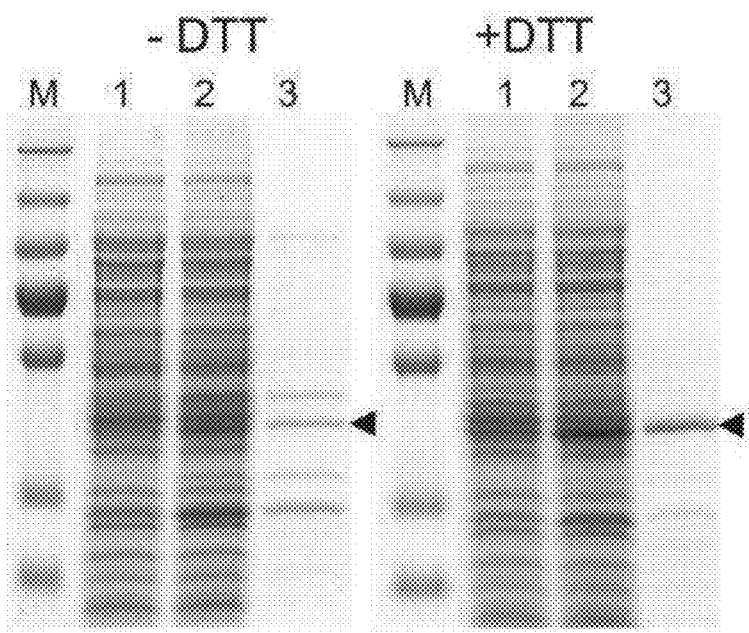
FIG. 20A  FIG. 20B

PROTEIN PRODUCTION

RELATED APPLICATIONS

This application is a continuation of co-pending U.S. application Ser. No. 13/354,748 filed Jan. 20, 2012, which claims priority to co-pending Great Britain Application No. 1101794.4, filed Feb. 2, 2011, which are hereby expressly incorporated by reference herein in their entirety.

FIELD OF INVENTION

The present invention relates to a method for recombinant protein/polypeptide production in host cells, wherein proper folding and soluble accumulation of the protein or polypeptide in the host cell is facilitated by addition of a reducing agent to the cultivation media.

BACKGROUND OF INVENTION

Recombinant proteins are extensively used in a variety of applications and therefore the demand for their efficient production is high. Recombinant proteins and polypeptides can be produced in heterologous host cells, with bacterial cells such as *Escherichia coli* (*E. coli*) being the most widely used hosts for recombinant protein production both for research and pharmaceutical applications. In particular, extreme *E. coli* cell robustness, fast and simple cultivation, easy genetic manipulation, enormous amounts of available physiological data and molecular biology tools are the reasons that make this microbe so widespread for recombinant protein production applications.

Despite these positive features, most heterologous protein production attempts in bacterial cells are ending with significantly reduced functional protein yields due target protein aggregation and/or improper folding. Many examples show that in general bacterial cell protein folding machinery is not adapted for a high level accumulation of "foreign" protein molecules with unusual features for the host: disulfide bonds, high hydrophobicity, etc.

Aggregation of heterologous protein in *E. coli* production hosts is a common phenomenon; a consequence of the inability of the host's folding machinery to cope with the rapidly accumulating target protein folding and/or to facilitate efficient stabilization of SH groups, or contribute to the formation and/or reorganization of correct disulfide bonds (see recent reviews Baneyx F et al. 2004 [1], Francis D M et. al 2010 [2]).

So far, the main research focus in this field is directed towards issues relating to correct disulfide bond formation, since these bonds are often important structural features of eukaryotic proteins. Direction of expressed recombinant protein into the cytoplasmic space of *E. coli* strains carrying trx/gor mutations or to the naturally oxidative periplasmic compartment are the most common approaches for improvement of heterologous protein disulfide bond formation (de Marco A et al. 2009 [3]). The efficiency of disulfide bond formation, or so-called disulfide shuffling, in *E. coli* periplasmic space is usually achieved by using in cultivation medium low molecular weight additives, which modify SH groups thereby aiding protein folding. For example, reduced/oxidized glutathione (GSH/GSSG) and arginine can easily penetrate the outer membrane and effect disulfide bond formation of recombinant proteins, propagation of which is directed to the periplasmic space. The utilization of low molecular weight agents GSH/GSSG for enhancement of disulfide bond formation in the periplasmic space for facilitated protein folding in respect of model proteins expressed and efficiently transported to the periplasmic space in a soluble state was disclosed by Wunderlich M et. al 1993 [4] and Walker K W et. al 1994 [5] (see also EP051065861).

Analogous, but more sophisticated in vivo folding/disulfide bond formation approaches for periplasmic space are based on the utilization of co-secreted prokaryotic disulfide oxidoreductases DsbA or DsbC as described in U.S. Pat. No. 5,639,635 and by Wunderlich M et al. 1993 [4], or eukaryotic protein disulfide isomerase (PDI) (Ostermeier M et al. 1996 [6]). Another example is where the presence of co-secreted cytoplasmic chaperones DnaJ or Hsp25 in combination with low molecular medium additives, such as L-arginine and 5 mM reduced GSH, facilitated folding of disulfide bonds containing proteins: a truncated version of tissue-type plasminogen activator, proinsulin and a single-chain antibody fragment, in the periplasmic space of *E. coli* BL21 (DE3) Schäffner J et al. 2001 [7].

Externally added components can also affect the redox state of disulfide bonds containing proteins in cytoplasm, as it was reported by Gill et al. 1998 [8]. Folding and activity of chloramphenicol acetyltransferase (CAT) in the cytoplasmic compartment was altered due to the presence of dithiothreitol (DTT) in the cultivation medium and resulted in enzyme inactivation but the mechanism underlying these changes is not clear. Further, the presence of DTT was indicated to have a negative effect on cellular physiology, causing in particular the elevated synthesis of host proteases.

There are several reports describing negative effect of reducing agent capable of diffusion through cell membrane, DTT, on disulfide bond formation/bond disruption in eukaryotic yeast and mammalian cells. The DTT when added to the cultivation medium, prevented disulfide bond formation of several proteins in ER and cytoplasmic space of living yeast cells thereby rendering those protein inactive. For example, Braakman and co-workers have demonstrated disruption of disulfide bond formation of influenza hemagglutinin (HA0) and induction of reduction of already oxidized HA0 in endoplasmic reticulum (ER) (Braakman I et al. 1992 [9]) by addition of DTT to the culture medium. Paunola and coworkers used DTT to confirm lack of disulfide bond formation during the folding of beta-lactamase (Paunola et al. 1998 [10]), as the addition of this reagent had no effect on enzyme activity. However, their work has also led scientists to believe that addition of DTT into cultivation medium has no effect on folding/activity of the proteins that do not contain disulfide bonds in their structure.

Another yeast cell related example was reported by Jämsä E and co-workers, where DTT-mediated disulfide bond disruption resulted in retention in the ER of vacuolar enzyme carboxypeptidase Y (CPY) and of secretory stress-protein hsp150. The proteins were reoxidized after DTT was washed out from the cells (Jämsä E et al. 1994 [11]).

The effects of DTT on disulfide bond formation in cytoplasmic space of mammalian cells were investigated by Valetti C et al. 1994 [12]. Mezghrani A and coworkers used DTT for manipulation of PDI redox state in experiments demonstrating oxidative folding capabilities of human Ero1-Lalpha and Ero1-Lbeta (hEROs) in living HeLa mammalian cells (Mezghrani A et al. 2001 [13]).

Raines discloses the dithiol catalysis approach, which aims to facilitate disulfide bond formation of heterologous protein in living cells (in vivo) and in vitro (U.S. Pat. No. 5,910,435). The method is based on utilization of organic dithiol molecules N,N'-bis(2-mercaptoacetyl)-1,2-diaminocyclohexane with specifically defined chemical properties:

pKa more than about 8.0 and a standard reduction potential of greater than about −0.25 volts. Such organic dithiol molecules were useful in catalysis of correct disulfide bond formation in the target protein in living yeast cells, which were deficient in protein disulfide isomerase (PDI) expression. The ability of organic dithiol molecules to catalyze disulfide bond formation in vitro was demonstrated on disulfide bond containing ribonuclease A.

However, few prior art documents address the issue of improving the production of proteins, such as ribonuclease inhibitor (RI), which contain a number of reduced cysteines that are vital to the function of the protein.

The members of the ribonuclease inhibitor group represent a specific subfamily within the large group of proteins with a very special protein fold-the Leucine Rich Repeat (LRR) proteins (Kobe B et.al 2001 [14]). LRR proteins share very interesting features, which make them a unique group of proteins. RI has an unusual non-globular flexible horseshoe like structure, which is highly conserved between different species. The core of ribonuclease inhibitor molecule is composed of hydrophobic 15-16 LRR motifs. Each of the LRR consists of a structural unit of 28 to 29 amino acids forming an α-helix and β-strand connected by loops (Dickson K A et al 2005 [15]). RI has a very high leucine content (18%), but also contains 30-32 cysteine residues (6.5-7%). In contrast to other LRR motif containing proteins where the cysteines are involved in maintaining protein structure (see e.g. Park H et. al. 2008 [16]), all cysteines in RI are reduced, a feature that is very important for its activity, i.e. substrate interaction. Oxidation of free SH groups in RI is highly cooperative and leads to enzyme inactivation and even denaturation (Fominaya J M et al. 1992 [17], Dickson K A et al. 2005 [15]).

Production of RI has been a challenge due to its flexible structure, amino acid repeats and reduced cysteines. In particular, the protein strongly aggregates if expressed in E. coli, even when folding takes place in the cytoplasm of bacteria, which is known to provide a reducing environment that prevents disulphide bond formation. Further, so far reported RI production attempts in yeast Saccharomyces cerevisiae (Vicentini A M et. al 1990 [18]) and in E. coli (Lee F S et al. 1989 [19], Klink T A, 2001 [20]) ended up with a low overall yield either due to low production levels and/or high RI insolubility. Recently, high amounts of soluble RI were produced in E. coli cells after the protein the MBP tag (≈32 kDa) was fused to the N-terminus. These results suggest that the addition of a tag may provide a solution to the problem of protein aggregation during production (Siurkus J et al. 2010 [21]).

Despite the existing body of research on improved bioproduction processes for disulfide bond forming heterologous proteins in E. coli, little is known about ways to improve yields of properly folded target recombinant proteins that possess reduced cysteines and, hence, their folding is not dependent on disulfide bond formation, or alternative ways to address the problem of insoluble protein accumulation. Therefore there is constant need in the industry for improved, more efficient methods for production of these recombinant proteins in host cell systems.

SUMMARY OF THE INVENTION

In a first aspect, the present invention provides a method for producing from host cells a heterologous polypeptide or protein comprising at least one cysteine residue in a reduced state, said method comprising: (i) culturing said host cells in a culture medium comprising a reducing agent; and (ii) recovering the heterologous polypeptide or protein comprising at least one cysteine residue in a reduced state from said host cells or from said culture medium, wherein said host cells comprise a nucleic acid encoding said heterologous protein or polypeptide, and wherein said reducing agent is capable of permeating the plasma membrane of the host cells.

In a second aspect, the present invention provides a method for producing from host cells a heterologous polypeptide or protein comprising at least one disulphide bond, said method comprising:
(i) culturing said host cells in a culture medium comprising a reducing agent to produce the heterologous polypeptide or protein with at least two cysteine residues in a reduced state; and
(ii) recovering the heterologous polypeptide or protein from said bacterial cells or from said culture medium, and (iii) exposing the heterologous polypeptide or protein to conditions which allow the at least two cysteine residues to form the at least one disulfide bonds, wherein said host cells comprise a nucleic acid encoding said heterologous protein or polypeptide, and wherein said reducing agent is capable of permeating the plasma membrane of the host cells.

In a further aspect, the present invention provides use of a reducing agent for host cell culture for the production of a heterologous polypeptide or protein from host cells, wherein the reducing agent is capable of permeating the plasma membrane of the bacterial cells and wherein the produced heterologous polypeptide or protein comprises at least one cysteine residue in a reduced state.

In a still further aspect the present invention provides use of a reducing agent for host cell culture for the production of a heterologous polypeptide or protein from the host cells, wherein the reducing agent is capable of permeating the plasma membrane of the host cell and wherein the heterologous polypeptide or protein comprises at least one disulfide bridge in its native conformation.

The present invention also provides use of a reducing agent for the production of a heterologous protein or polypeptide from host cells wherein the heterologous protein or polypeptide is a ribonuclease inhibitor or a Dnase.

The present inventors have found that the use of a membrane permeating reducing agent in the culture media of host cells has a significant positive effect on the production of heterologous proteins or peptides whose native conformation comprises cysteine residues in a reduced state. The reducing agent can enhance production of functional proteins/polypeptides in both the cytoplasmic and periplasmic compartments. These results are particularly surprising given the work of Paunola and co-workers which indicates that the addition of the reducing agent, dithiothreitol, into cultivation medium has no effect on folding/activity of the proteins that do not contain disulfide bonds in their structure. Further, the present inventors have surprisingly found that the membrane permeating reducing agent can assist in the soluble accumulation of heterologous proteins/polypeptides in the host cells and can be used as part of a method to produce heterologous proteins/polypeptides which comprise disulphide bonds in their native conformations.

BRIEF DESCRIPTION OF THE FIGURES

The invention will be described in further detail, by way of example only, with reference to the accompanying drawings in which:

FIGS. 6A, 6B, 6C and 6D show SDS-PAGE images of protein fractions using cytoplasmic production construct *E. coli* RV308 pCUlac His$_6$-RI produced at 37° C. in the absence (FIG. 6A) and presence (FIG. 6B) of DTT in the medium, and produced at 22° C. in the absence (FIG. 6C) and presence (FIG. 6D) of DTT in the medium.

FIGS. 11A and 11B show RI activities in *E. coli* crude extracts of RV308 pCUlac pelB-RI (FIG. 11A) and RV308 pCUlac-His$_6$-RI (FIG. 11B) constructs, from samples of batch and fed-batch bioreactor cultivations in the absence and presence of DTT.

FIGS. 18A, 18B, 18C and 18D show agarose gel images after DNA electrophoresis, with samples generated from soluble protein extracts (FIGS. 18A, C) and commercial DnaseI (FIG. 18B, D) incubation with pUC57 DNA.

FIG. 19 shows agarose gel image after DNA electrophoresis, with samples generated from soluble protein extracts incubation with A phage.

FIGS. 20A and 20B show SDS-PAGE images of protein fractions using *E. coli* production construct pACY184-TT-SssI in the absence (FIG. 20A) and presence (FIG. 20B) of DTT.

DETAILED DESCRIPTION OF THE INVENTION

Figure 1A:
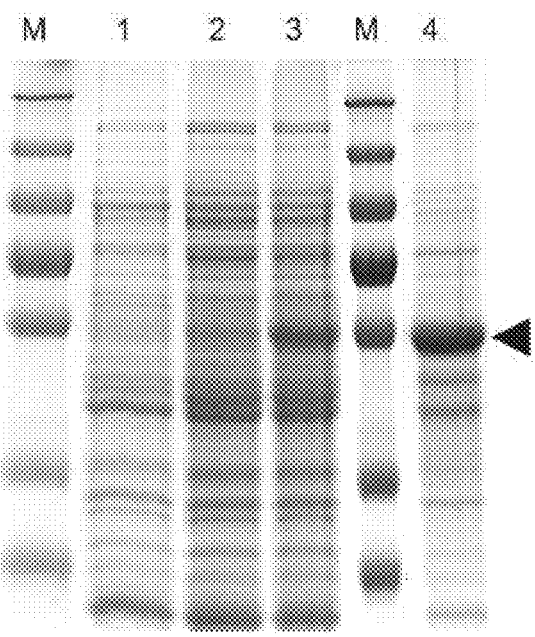
FIGS. 1A and 1B show SDS-PAGE images of protein fractions using periplasmic production construct *E. coli* RV308 pCUvar-malE-RI in the absence (FIG. 1A) and presence (FIG. 1B) of DTT.

As indicated above, the present invention concerns a method to improve production of a polypeptide or protein via heterologous expression in a host cell culture.

Polypeptide/Protein

In the first aspect of the invention and related uses the polypeptide or protein produced in the method and use of the present invention (herein, the "heterologous", "target" or "recombinant" polypeptide or protein) is one which comprises (in its native conformation, or in its desired conformation) at least one cysteine residue, and preferably at least two cysteine residues, in a reduced state, i.e. the cysteine residue(s) within the amino acid sequence of the polypeptide or protein are present as cysteine residues rather than as part of a dimeric cystine. (The native or wild-type structures of these polypeptides/proteins is not dependent on disulfide bonds formation; the native protein conformation or native state being one in which the protein possesses complete biological functionality). In particular, the polypeptide or protein is one whose native conformation, biological activity, and/or accumulation in soluble fraction (cytoplasmic and/or periplasmic) is dependent on cysteine content and state. Preferably the activity of the polypeptide or protein is reduced on oxidation of its cysteine residues.

Further, the polypeptide or protein is one whose native (wild-type) conformation comprises a hydrophobic core.

In particular, the present inventors have found that for recombinant protein production in host cells, proper folding and soluble accumulation of recombinant proteins possessing reduced or partially reduced population (reduced/oxidized) of cysteine residues in cytoplasmic and periplasmic compartments is facilitated by addition of a reducing agent to the cultivation media.

The protein or polypeptide may be of eukaryotic or prokaryotic origin, and/or may be a chimeric polypeptide or protein (a fusion protein). In one embodiment the protein is an enzyme. In a preferred embodiment the protein is a ribonuclease inhibitor (RI), an RNA polymerase, a kinase, an enterokinase, a methyltransferase, or a fusion protein comprising at least a part of said enzymes which retains activity. More particularly, the enzymes can be fusion protein rpoB-lysC (*E. coli*), bovine enterokinase (EK) catalytic subunit fusion with thioredoxin-(Trx-EK), and prokaryotic SssI methyltransferase.

In a particularly preferred embodiment of the first aspect of the invention the protein is a ribonuclease inhibitor. These proteins are characterized by a high amount of reduced cysteines, which are vital for the function of the protein.

In the second aspect of the invention and related uses the polypeptide or protein produced in the method and use of the present invention (herein, the "heterologous", "target" or "recombinant" polypeptide or protein) is one which comprises (in its native conformation, or in its desired conformation) one or more cysteine residues which form one or more disulphide bonds, preferably fewer than five disulfide bonds, more preferably two or one disulfide bonds. In an embodiment of this aspect of the invention the polypeptide or protein is one which comprises in its native conformation or desired conformation a hydrophobic core. As above, the native conformation is the wild-type structure of the and/or the molecular state at which the protein posesses (preferably complete) biological functionality.

In a preferred embodiment of this aspect of the invention the polypeptide or protein comprises a Dnase, in particular, Dnase I or Dnase II. Most preferably the protein is Dnase I.

Host Cells

The cells for use in the present invention are those that are suitable as host cells for the expression of the heterologous protein or polypeptide. They can be prokaryotic or eukaryotic. Possible eukaryotic cells are those of phylamentous fungi, *Aspergillus oryzae, Saccharomyces cerevisiae*. Preferably, however, the host cells are prokaryotic, more preferably bacterial cells. The bacteria can be Gram-negative or Gram-positive bacteria. *Escherichia coli* is preferred. In this regard, strains such as BL21, K12, ER2566, JM109, HM174 can be used. Alternative bacterial cells are well known in the art. Examples are *Bacillus brevis, Bacillus megaterium, Bacillus subtilis*, and *Caulobacter crescentus*.

In the methods and uses of the present invention the host cell comprises nucleic acid encoding the heterologous protein or polypeptide. The nucleic acid is in a form which permits its expression by the host cell, such that culturing the host cell under the appropriate conditions allows the expression of the nucleic acid and subsequent production of the heterologous protein or polypeptide via translation. After translation, i.e. in step (i) of the methods of the present invention, the heterologous protein or polypeptide accumulates in the host cell in soluble form.

Usually, host cells carrying the nucleic acid are prepared by transformation with expression vectors comprising the nucleic acid. Methods of transformation and suitable vectors are well known in the art. In particular, plasmids can be used. Generally the vectors carry, in addition to the nucleic acid sequence encoding the protein or polypeptide, an origin of replication and a promoter system, to control the strength and duration of transcription. Usually, the promoter system is inducible, to allow transcription to be turned on and off at suitable times during the culturing of the host cell. Promoter systems are known in the art and examples are described in Francis D M et. al 2010 [2]. Suitable bacterial systems are T7 expression system or the pASK system.

Where the host cell is a prokaryotic cell which comprises cytoplasmic and periplasmic compartments the produced heterologous polypeptides or proteins can be folded in either of these compartments. The movement of the produced proteins to the periplasmic space can be achieved using an export sequence as a fusion tag.

In a preferred embodiment of the invention, however, where the host cell is a prokaryotic cell the nucleic acid encoding said heterologous protein or polypeptide does not encode a fusion tag to direct export of the translated polypeptide or protein to the periplasm.

Reducing Agent

The reducing agent used in the methods and uses of the present invention is one which is capable of permeating the membranes of the host cells (e.g. the inner and outer plasma membranes of bacterial cells). In other words, the reducing agent is capable of entering the cytoplasm of the host cell.

Usually the reducing agent should be of low molecular weight, e.g. less than 320 g/mol, and more preferably less than 200 g/mol, still more preferably less than 175 g/mol. Alternatively, or in addition, the reducing agent can be defined as one which has a reduction potential stronger (lower) than $-0.1$V at pH 7 and 25° C., more preferably stronger than $-0.2$V at pH 7 and 25° C. Still further, the reduction potential can be defined as being equal or stronger than the reduction potential of dithiothreitol±10%.

The reducing agent is an SH group modifying agent and is preferably one which comprises a thiol group, more preferably one which comprises at least two thiol groups. Most preferably the reducing agent is dithiothreitol (DTT) or dithioerythritol (DTE) or derivatives thereof comprising a substituted carbon. Examples of other low molecular weight reducing agents are amino acids (e.g. cysteine, selenocysteine), alcohols (mercaptoethanol), di-tri-peptides, organic compounds, lipoic acid and TCEP (tris(2-carboxyethyl) phosphine) phospine. In a preferred embodiment the reducing agent is not glutathione.

The reducing agent is present in the culture medium at an amount that is sufficient to improve the production (and folding and soluble accumulation) of the heterologous protein or polypeptide, but which is non-toxic to the host cells. In a preferred embodiment where the reducing agent is dithiothreitol this is present in the culture medium at a concentration of 2 to 18 mM. In an alternative embodiment, where the reducing agent is not dithiothreitol, the reducing agent is present in an amount that provides the culture medium with an equivalent reduction potential to one comprising 2 to 18 mM dithiothreitol.

Culturing Step

The host cells can be cultured in batch and fed-batch culture growth modes, in shake flasks and/or in stirred bioreactors, using growth media which is known in the art. The reducing agent can be premixed with the growth media, or can be added to the growth media, to acheive the required concentration. In particular, the reducing agent can be added to the medium at induction of recombinant protein production and/or during the course of recombinant protein production. For example, in some cases the medium may be supplemented with reducing agent 2 hours after induction of synthesis. Where the reducing agent is reduced DTT, this may be added to the culture medium as dry powder or as a concentrate solution.

In preferred embodiments of the present invention the step of culturing the bacteria to express the heterologous proteins or polypeptides is conduced at low cultivation temperatures and/or at micro-aerobic growth conditions. In particular, the method of the invention may comprise a step during which the bacteria are cultured at a temperature below 37° C., and preferably at a temperature between 15 and 30° C. Preferably, cultivation temperature should be decreased at the target protein synthesis induction point. Further, the culturing may involve a step in which the concentration of oxygen in the medium is maintained at less than 1%, more preferably less than 0.8%. This can be achieved by reducing air flow to the culture.

For the ribonuclease inhibitor, synthesis in *E. coli* bacterial cells in fed-batch shake flask may be performed using gel based EnBase® system. Glucose release for substrate limited growth may be in the range of 12 AGU $L^{-1}$ in the cultivation medium (as described by Siurkus et.al 2010, [21]). RI synthesis from the selected expression platforms may be induced at substrate limited mode corresponding to $\mu \approx 0.22$ $h^{-1}$.

Batch and fed-batch periplasmic and cytoplasmic RI production with DTT-facilitated folding may be performed in stirred bioreactor as well. During batch cultivations RI synthesis in the cytoplasmic and periplasmic compartments may be induced at maximum specific growth rate ($\mu$), in particular case $-\mu \approx 0.45$ $h^{-1}$. In all fed-batch production processes RI production may be induced preferably in the glucose limited growth phase with exponential feeding at $\mu \approx 0.22$ $h^{-1}$. After induction the feeding rate may be further increased according to the predetermined function with the same $\mu$ set as before induction. Also DTT may be added at the time of induction and concomitantly the temperature may be decreased from 37° C. to 22° C.

According to the present invention, DTT oxidation analysis in the cultivation medium shows that even at micro aerobic conditions more than 50% of DTT are oxidized during bioreactor cultivation already after 3 h. Compared to bioreactor, in the shake flasks DTT oxidation rate is very low—only 10%, during 4 synthesis hours. Therefore the highest soluble and active RI amount after synthesis in stirred bioreactor may be obtained by applying repeated (3 times) DTT addition approach, preferably starting at 2 hours after RI synthesis induction. Additionally, in order to prevent rapid DTT oxidization, in all processes at the DTT addition point the air flow may be reduced from 30 L $min^{-1}$ to 2-3 L $min^{-1}$ to maintain the oxygen concentration in the medium close to zero. At reduced air flow rate the addition of DTT provokes clear positive effect with highest yields in both the periplasmic and the cytoplasmic expression systems.

Promoter Systems

In a further preferred embodiment of the present invention the promoter system, which controls the expression of the nucleic acid encoding the protein or polypeptide, comprises genetic control elements (e.g. a promoter and ribosome binding site(s)) which determine weak expression levels, such as the pCU-promoter (see Siurkus et al. 2010 [21]), and the -var and -lac ribosome binding sites for prokaryotic systems. In particular, these weak promoter systems are those that provide for expression levels at 15% or less, preferably 10% or less, of the total cellular protein. Suitable promoter systems for prokaryotic cells are described in Examples 1 to 4 below (including lac promoter and T7 RBS). Further, the expression can be controlled through the use of reduced amounts of different inducers, for example IPTG, arabinose, anhidro-tetracycline and tetracycline.

Other appropriate promoter/inducer systems are known in the art (for example as described in Kraft et al., [26] and Šiurkus et al., [23]).

In particular, the present inventors have found that the effect of a reducing agent, and in particular DTT, on soluble RI accumulation and activity is significantly enhanced at the low synthesis temperature (preferably below 30° C.) and/or in *E. coli* constructs harboring weak genetic elements determining target protein expression. In particular, this is shown in Examples 1 to 4 described below.

Molecular Chaperones

In a still further preferred embodiment of the present invention the bacteria further comprises vector constructs determining co-expression of fold-aiding molecular chaperone proteins at elevated synthesis levels. In particular, molecular chaperones can be co-expressed when a strong promoter system, like a T7 promoter, is used to express the nucleic acid encoding the target polypeptide or protein.

Molecular chaperones suitable for specific bacterial cells are known in the art. For example, the DnaK-DnaJ-GrpE or the GroEL-GroES systems can be used, in prokaryotic organisms, and *E. coli* in particular.

Preferably the bacterial cells are induced to express the molecular chaperones prior to induction of the target polypeptide/protein expression. For example, the chaperone production may be induced at 1-2 hours prior to induction of target polypeptide/protein synthesis.

Recovery Step

After synthesis the heterologous polypeptide or protein comprising the at least one cysteine residue in a reduced state can be recovered from the host cells by methods which are known in the art. In particular, this step is usually performed with in the presence of a reducing agent, such as DTT.

In the second aspect of the present invention and related uses the method further comprises a step of allowing the at least two reduced cysteine residues to form at least one disulphide bond. This step can be conducted as part of the step of recovering the produced polypeptide/protein, or it can be conducted subsequently to the recovery step. In a preferred embodiment where the heterologous protein or polypeptide is a Dnase the reduced cysteines can be allowed to form disulphide bridges during the recovery step through exposure to calcium ions. However, other methods of inducing the formation of disulfide bridges are well known in the art.

The invention will now be described by way of example only, with reference to the following Examples,

EXAMPLE 1

Periplasmic folding improvement of Ribonuclease inhibitor (RI) from lungs of dormouse, *Muscardinus avellanarius* (~49 kDa). (This protein shows a homology of 79-82% to well characterized RNase ribonuclease/angiogenin inhibitors from human (hRI), rat (rRI), mouse (mRI) and pigs (pRI)).

Preparation of Target Protein Expression Platforms.

The expression strain *E. coli* K-12 RV308 (ATCC 31608) and isogenic RV308 DsbA deficient strain were transformed with RI periplasmic expression vectors (pCUvar and pCU-lac) containing well known periplasmic leader peptides: malE, ompA, phoA and pelB (for detailed vector description see paper by Kraft et al. 2007) using calcium temperature shock method.

The transformants were plated on LB agar containing chloramphenicol (30 µg $mL^{-1}$). The cell stock was produced after 8 h of recombinant strain cultivation in 10 mL of LB medium in 100 mL shake flasks at 37° C. and 220 rpm. All culture suspensions with $OD_{600}$ of 4±0.2 were mixed with an equal volume of sterile 50% glycerol solution to achieve a final glycerol concentration of 25%. The glycerol culture suspensions were aliquoted into sterile PCR strips and stored at −70° C.

Ribonuclease Inhibitor Expression in the Batch Shake Flasks.

The inoculums for batch protein production in the shake flasks were prepared by overnight batch cultivation of the selected clones in 500 mL shake flasks with 50 ml of MSM medium (Siurkus et al, 2010) containing 10 g $L^{-1}$ of glucose. For protein production 5% of the corresponding inoculum culture was transferred to fresh MSM medium containing the same amount of glucose at a final volume of 500 mL in 2 L baffled Erlenmeyer shake flasks. Cultures were cultivated at 37° C., 180 rpm, until they reached the induction point, corresponding to a cell density of $OD_{600}$=1±0.05 ($\mu \approx 0.35$ $h^{-1}$). Induction was performed by addition of IPTG (1 M) to a final concentration of 0.2 mM. DTT was added to the cultivation medium at the RI induction point as dry powder to achieve the working final concentration of 2 mM to 18 mM. Cytoplasmic and periplasmic expressions were carried out for 4 h at 22° C. at a shaking rate of 180 rpm.

Protein Analysis

Cell samples harvested from flasks or bioreactor cultivations were resuspended in lysis buffer with the following biomass to buffer ratio: 1 g of biomass with 10 mL of lysis buffer (50 mM Tris-$H_3PO_4$ pH 8.0, 0.1% Triton X-100, 2 mM EDTA, 1 mM PMSF, 15 mM DTT, 10% propyleneglycol and 0.1 mg $mL^{-1}$ lysozyme). After 30 min of lysis at +4° C. the biomass was sonicated for 60 sec (Vibra cell™, Sonic and Materials Inc., 6 mm diameter probe tip) at 4° C. Soluble and insoluble protein fractions were separated by centrifugation for 30 min, 14000 rpm, 4° C. The total protein fraction represents cellular debris suspension (crude extract) before centrifugation. After centrifugation the insoluble protein pellet was additionally washed and resuspended in the original volume of lysis buffer without lysozyme.

The periplasmic protein fractions were extracted by the standard osmotic shock procedure. Therefore after centrifugation the cell pellet was resuspended in 5 mL of ice cold solution, containing 20% (w/v) sucrose, 100 mM Tris-$H_3PO_4$ (pH 8.0), and 2 mM $Na_2$EDTA. After incubation for 10 min at +4° C. cells were harvested by centrifugation at 10,000 rpm for 10 min and +4° C. After removal of the supernatant the cell pellet was again resuspended in 5 mL of ice cold deionized water, containing 15 mM of DTT. After another incubation for 10 min and centrifugation the supernatant (containing the target protein) was supplemented with 2.0 ml of buffer (250 mM Tris-$H_3PO_4$ pH 8.0, 0.4% Triton X-100, 8 mM $Na_2$EDTA, 4 mM PMSF, 30% propylene glycol).

The amount of active RI in the soluble fraction was determined by an activity assay described by Blackburn et al. 1977 and 1979.

Samples for SDS-PAGE separation were prepared as follows: 20 μL of protein sample (total soluble, insoluble, protein suspensions), 25 μL of 4×SDS-PAGE loading buffer (Fermentas), 5 μL of 20×DTT (Fermentas) and 50 μL of deionized water to obtain a final sample volume of 100 μL. Samples were heated for 15 min at 95° C. Ten μL of sample was applied to each lane of a 10% SDS-PAGE gel.

The N-terminal amino acid sequence of processed RI was determined by the Edman degradation procedure in Biocentrum Ltd. (Krakow, Poland) from insoluble protein fraction sample after RI production in the presence of DTT in the medium and subsequent separation on an 8% SDS-PAGE gel.

Figure 1B:
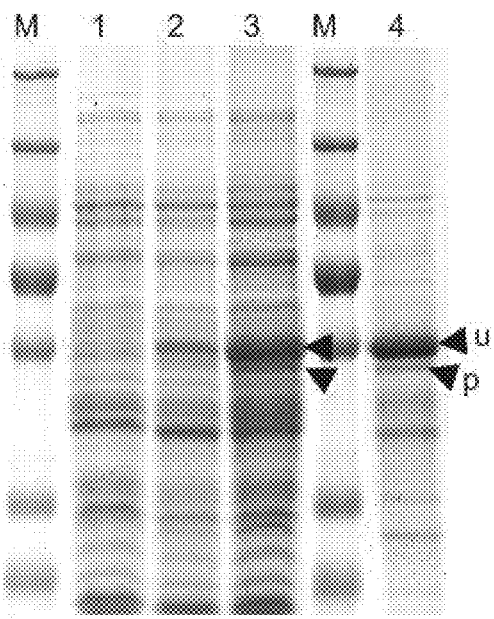

FIGS. 1A-B show 10% SDS-PAGE images of normalized to equal amounts protein fractions of periplasmic production construct: E. coli RV308 pCUvar-malE-RI. FIG. 1A represents SDS-PAGE gel image with protein fractions after RI production with no DTT in the medium and FIG. 1B with 12 mM DTT. Numbered lanes in the SDS-PAGE gels represents 1—total protein fraction 10 min before RI synthesis induction, 2, 3 and 4—soluble, total and insoluble protein fractions 4 h after RI synthesis induction. Protein size marker was PageRuler™ Protein Ladder Plus (Fermentas). Arrow ◀ (FIG. 1A) and arrow ◀u (FIG. 1B) indicates unprocessed RI (53 kDa); arrow ◀p (FIG. 1B) indicates processed RI (50 kDa). All cultures were initially started at 37° C., induced with 0.2 mM of IPTG and shifted to the respective temperature at the time of RI induction.

Figure 2A:
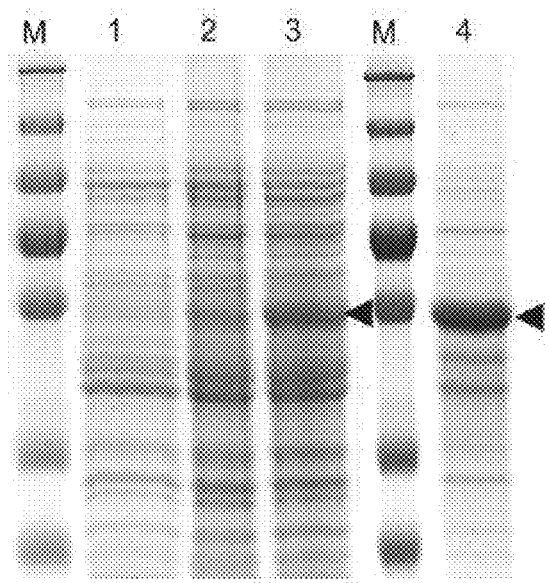
FIGS. 2A and 2B show SDS-PAGE images of protein fractions using periplasmic production construct *E. coli* RV308 pCUvar-ompA-RI in the absence (FIG. 2A) and presence (FIG. 2B) of DTT.
Figure 2B:
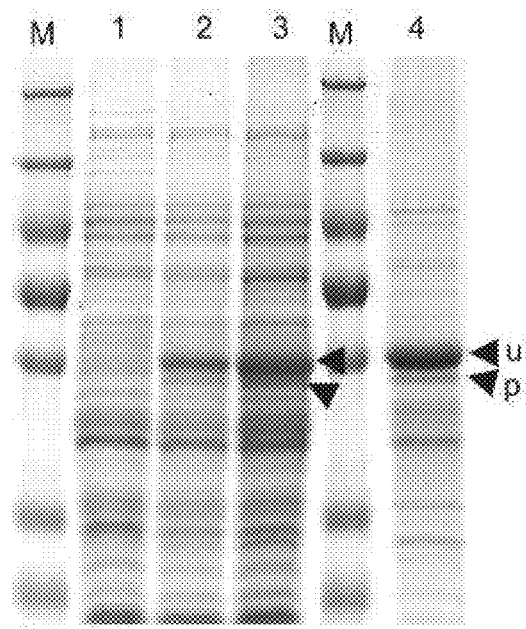

FIGS. 2A-B show 10% SDS-PAGE images of normalized to equal amounts protein fractions of periplasmic production construct: E. coli RV308 pCUvar-ompA-RI. FIG. 2A represents SDS-PAGE gel image with protein fractions after RI production with no DTT in the medium, and FIG. 2B with 12 mM DTT. Numbered lanes in the SDS-PAGE gels represents 1—total protein fraction 10 min before RI synthesis induction, 2, 3 and 4—soluble, total and insoluble protein fractions 4 h after RI synthesis induction. Protein size marker was PageRuler™ Protein Ladder Plus (Fermentas). Arrow ◀ (FIG. 2A) and arrow ◀u (FIG. 2B) indicates unprocessed RI (53 kDa); arrow ◀p (FIG. 2B) indicates processed RI (50 kDa). All cultures were initially started at 37° C., induced with 0.2 mM of IPTG and shifted to the respective temperature at the time of RI induction.

Figure 3A:
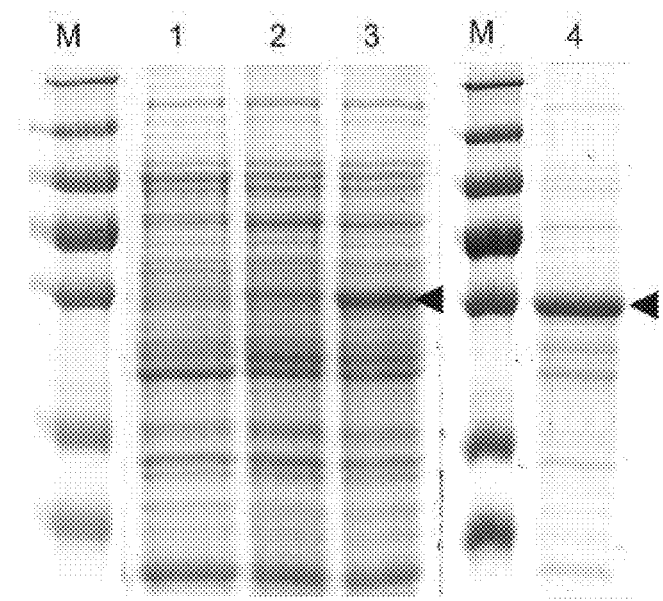
FIGS. 3A and 3B show SDS-PAGE images of protein fractions using periplasmic production construct *E. coli* RV308 (dsbA$^-$) pCUvar-malE-RI in the absence (FIG. 3A) and presence (FIG. 3B) of DTT.
Figure 3B:
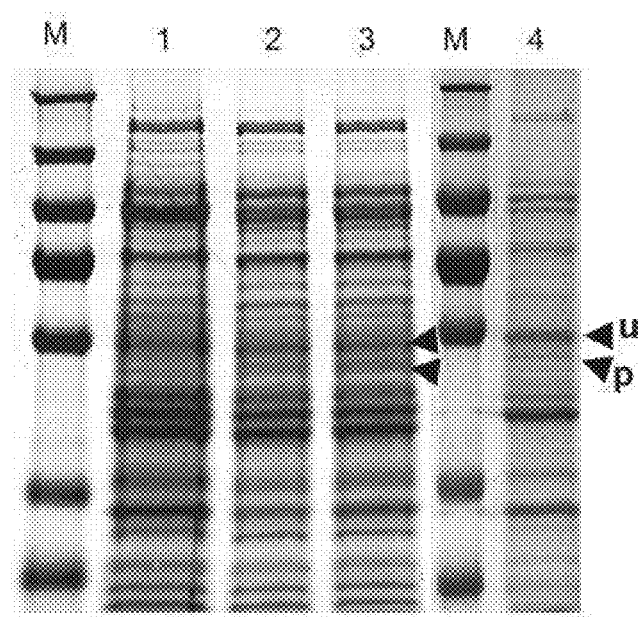

FIGS. 3A-B show 10% SDS-PAGE images of normalized to equal amounts protein fractions, of DsbA deficient, periplasmic production construct: E. coli RV308 (dsbA) pCUvar-malE-RI. FIG. 3A represents SDS-PAGE image with protein fractions after RI production with no DTT in the medium, and FIG. 3B with 12 mM DTT. Numbered lanes in the SDS-PAGE gels represents: 1—total protein fraction 10 min before RI synthesis induction, 2, 3 and 4 -soluble, total and insoluble protein fractions 4 h after RI synthesis induction. Protein size marker was PageRuler™ Protein Ladder Plus (Fermentas). Arrow ◀ (FIG. 3A) and arrow ◀u (FIG. 3B) indicates unprocessed RI (53 kDa); arrow ◀p (FIG. 3B) indicates processed RI (50 kDa). All cultures were initially started at 37° C., induced with 0.2 mM of IPTG and shifted to the respective temperature at the time of RI induction.

Figure 4A:
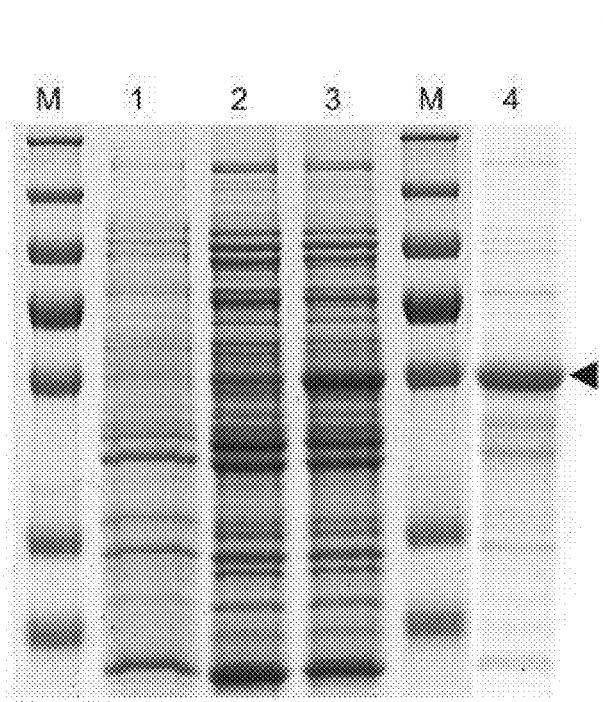
FIGS. 4A and 4B show SDS-PAGE images of protein fractions using periplasmic production construct *E. coli* RV308 (dsbA$^-$) pCUvar-ompA-RI in the absence (FIG. 4A) and presence (FIG. 4B) of DTT.
Figure 4B:
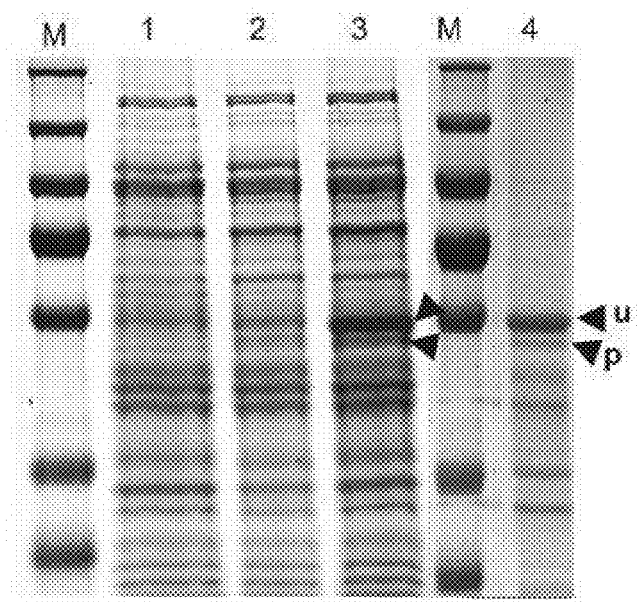

FIGS. 4A-B show 10% SDS-PAGE images of normalized to equal amounts protein fractions of DsbA deficient E. coli periplasmic production construct: RV308 (dsbA⁻) pCUvar-ompA-RI. FIG. 4A represents SDS-PAGE image with protein fractions after RI production with no DTT in the medium, and FIG. 4B with 12 mM DTT. Numbered lanes in the SDS-PAGE gels represents: 1—total protein fraction 10 min before RI synthesis induction, 2, 3 and 4—soluble, total and insoluble protein fractions 4 h after RI synthesis induction. Protein size marker was PageRuler™ Protein Ladder Plus (Fermentas). Arrow ◀ (FIG. 4A) and arrow ◀u (FIG. 4B) indicates unprocessed RI (53 kDa); arrow ◀p (FIG. 4B) indicates processed RI (50 kDa). All cultures were initially started at 37° C., induced with 0.2 mM of IPTG and shifted to the respective temperature at the time of RI induction.

Figure 5A:
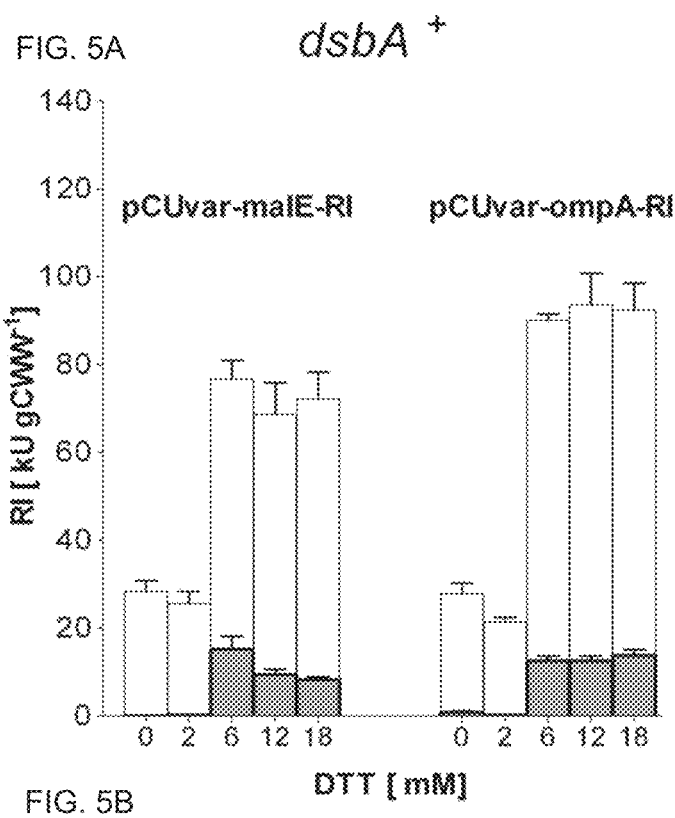
FIGS. 5A and 5B show RI protein activities in total soluble and periplasmic fractions in different *E. coli* RV308 constructs (FIG. 5A) and in isogenic RV308 dsbA$^-$ strain constructs (FIG. 5B) in the absence or presence of DTT in medium.
Figure 5B:
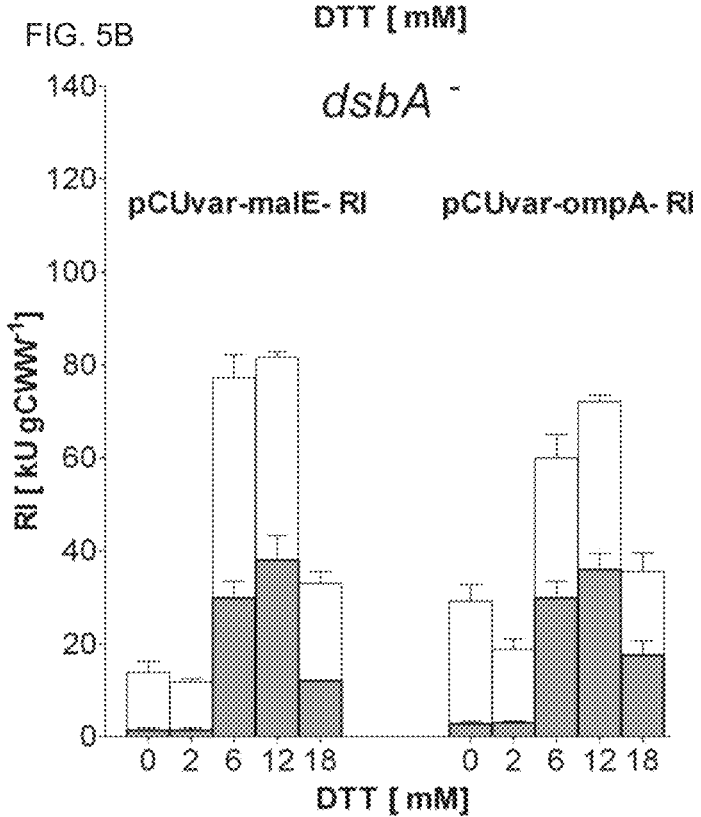

FIG. 5A shows RI protein activities in total soluble and periplasmic fractions in kilo units per gram of wet cell weight [kU $(gCWW)^{-1}$] after 4 hours of batch RI production in different E. coli RV308 constructs at 22° C. with 0, 2, 6, 12 and 18 mM of DTT in medium. All cultures were initially started at 37° C. in MSM medium containing 10 g $L^{-1}$ of glucose, RI production was induced with 0.2 mM of IPTG and shifted to the respective temperature at the time of RI induction. FIG. 5B shows RI protein activities in total soluble and periplasmic fractions in kilo units per gram of wet cell weight [kU $(gCWW)^{-1}$], after RI production in isogenic RV308 dsbA⁻ strain constructs, at above listed conditions. Gray-filled bars represent periplasmic RI activity and open white bars represent total RI activity. In each of FIGS. 5A and 5B, the left-hand group of bars represents protein production using pCUvar-malE-RI, and the right-hand group of bars represents protein production using pCUvar-ompA-RI.

Conclusions from Example 1

(i) The DTT increased accumulation of processed RI in the periplasmic space of E. coli RV308 independently from the state of dsbA gene activity (active vs. inactive).
(ii) The RI activity in the periplasmic space was positively affected by supplementation of the cultivation medium with DTT in the course of RI production, independently from the state of dsbA gene activity (active vs. inactive). However obtained RI activity was significantly higher in the periplasmic space of dsbA minus strain as compared to isogenic—dsbA positive strain.
(iii) Unprocessed RI accumulation in cytoplasmic space of E. coli RV308 was positively affected by medium supplementation with DTT, independently from the state of dsbA gene activity (active vs. inactive).
(iV) Total RI activity was positively affected by medium supplementation with DTT independently from the state of dsbA gene activity (active vs inactive).

EXAMPLE 2

Improvement of cytoplasmic folding of Ribonuclease inhibitor (RI) from lungs of Muscardinus avellanarius.
Preparation of Target Protein Expression Platform.

The expression strain E. coli K-12 RV308 (ATCC 31608) was transformed with cytoplasmic expression vector RV308/pCUlac-His$_6$-RI (Siurkus et. al 2010) and plated on LB agar containing chloramphenicol (30 µg mL$^{-1}$). The cell stock was produced after 8 h of recombinant strain cultivation in 10 mL of LB medium in 100 mL shake flasks at 37° C. and 220 rpm. All culture suspensions with OD$_{600}$ of 4±0.2 were mixed with an equal volume of sterile 50% glycerol solution to achieve the final glycerol concentration of 25%. The glycerol culture suspensions were aliquoted into sterile PCR strips and stored at −70° C.

Batch Mode Cultivations in the Shake Flasks

The inoculums for batch protein production in the shake flasks were prepared by overnight batch cultivation of the selected clones in 500 mL shake flasks with 50 ml of MSM medium at 37° C. containing 10 g L$^{-1}$ of glucose. For protein production 5% of the corresponding inoculum culture was transferred to fresh MSM containing the same amount of glucose at the final volume of 200 mL in 1 L baffled Erlenmeyer shake flasks. Cultures were cultivated at 37° C. and 180 rpm until they reached the induction point, corresponding to a cell density of OD$_{600}$=1±0.05 (µ≈0.35 h$^{-1}$). Induction was performed by addition of IPTG (1 M) to a final concentration of 0.2 mM. DTT was added to the cultivation medium at the RI induction point as dry powder to achieve 12 mM final concentration. Cytoplasmic was carried for 4 h at 22° C.-37° C. at the shaking rate of 180 rpm.

Protein Analysis.

Cell samples harvested from flask or cultivations were resuspended in lysis buffer with the following biomass to buffer ratio: 1 g of biomass with 10 mL of lysis buffer (50 mM Tris-H$_3$PO$_4$ pH 8.0, 0.1% Triton X-100, 2 mM EDTA, 1 mM PMSF, 15 mM DTT, 10% propyleneglycol and 0.1 mg mL$^{-1}$ lysozyme). After 30 min of lysis at +4° C. the biomass was sonicated for 60 sec (Vibra cell™, Sonic and Materials Inc., 6 mm diameter probe tip) at +4° C. The soluble and insoluble protein fractions were separated by centrifugation for 30 min, 14000 rpm, 4° C. The total protein fraction represents cellular debris suspension (crude extract) before centrifugation. After centrifugation the insoluble protein pellet was additionally washed and resuspended in the original volume of lysis buffer without lysozyme.

The amount of active RI in the soluble fraction was determined by an activity assay described by Blackburn et al. 1977 and 1979.

Samples for SDS-PAGE separation were prepared as follows: 20 µL of protein sample (total soluble, insoluble, protein suspensions), 25 µL of 4×SDS-PAGE loading buffer (Fermentas), 5 µL of 20×DTT (Fermentas) and 50 µL of deionized water to obtain a final sample volume of 100 µL. Samples were heated for 15 min at 95° C. Ten µL of sample was applied to each lane of a 10% SDS-PAGE gel.

FIGS. 6A-D show 10% SDS-PAGE images of protein fractions, normalized to equal amounts, of cytoplasmic production construct: E. coli RV308 pCUlac His$_6$-RI. FIGS. 6A and B represent SDS-PAGE images with protein fractions after RI production at 37° C. with no DTT in the medium (FIG. 6A) and with 12 mM DTT (FIG. 6B). FIGS. 6C and D represent SDS-PAGE images with protein fractions after RI production at 22° C. with no DTT in the medium (FIG. 6C) and with 12 mM DTT (FIG. 6D). Numbered lanes in the SDS-PAGE gels represents 1—total protein fraction 10 min before RI synthesis induction, lanes 2, 3 and 4—soluble, total and insoluble protein fractions 4 h after RI synthesis induction. Protein size marker was PageRuler™ Protein Ladder Plus (Fermentas). Arrow ◀ (FIG. 6A-D) indicates His$_6$-RI (52 kDa). All cultures were initially started at 37° C., induced with 0.2 mM of IPTG and shifted to the respective temperature at the time of RI induction.

Figure 7:
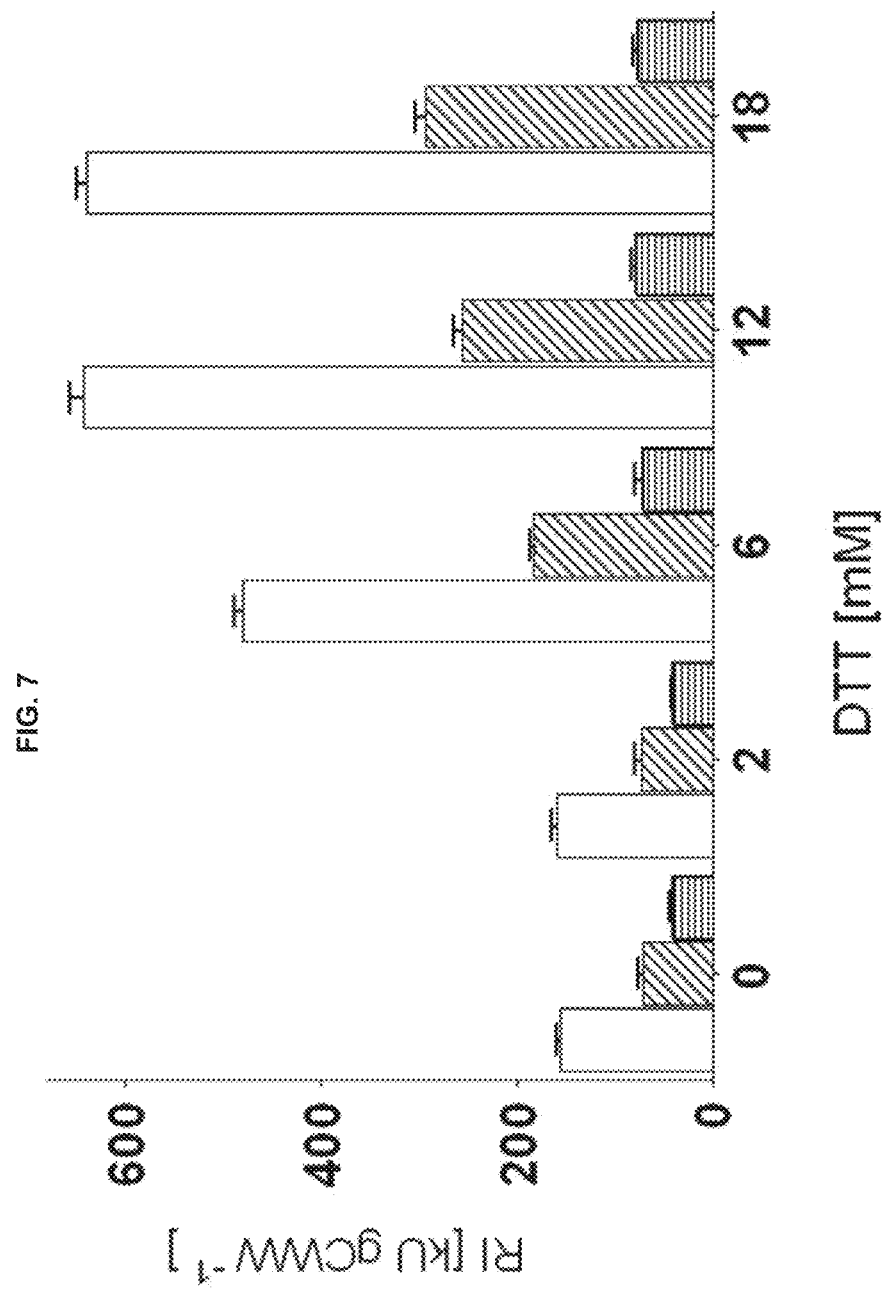
FIG. 7 shows protein activities in total soluble fractions in *E. coli* RV308 pCUlac-His$_6$-RI construct produced at 22° C., in the absence or presence of DTT in the medium.

FIG. 7 shows RI protein activities in total soluble fractions in kilo units per gram of wet cell weight [kU (gCWW)$^{-1}$] after 4 hours of batch cytoplasmic RI production in E. coli RV308 pCUlac-His$_6$-RI construct at 22° C. (open bars), 30° C. (diagonally striped bars), and 37° C. (horizontally striped bars), with 0, 2, 6, 12 and 18 mM of DTT in the medium. All cultures were initially started at 37° C. in MSM medium containing 10 g L$^{-1}$ of glucose, induced with 0.2 mM of IPTG and shifted to the respective temperature at the time of RI induction.

Conclusions from Example 2:

(i) Cytoplasmic RI accumulation in the soluble protein fraction was significantly improved by supplementation of cultivation medium with DTT during RI production course.
(ii) RI activity in E. coli cytoplasmic space was significantly improved due to supplementation of cultivation medium with DTT during RI production course.
(iii) The DTT effect on soluble RI accumulation in the cytoplasmic space and activity (folding) was dependent on RI synthesis temperature.

EXAMPLE 3

Periplasmic and cytoplasmic folding improvement of Ribonuclease inhibitor (RI) from lungs of Muscardinus avellanarius.
Preparation of Target Protein Expression Platforms.

The RI expression periplasmic (RV308 pCUlac pelB RI) and cytoplasmic (RV308 pCUlac-His$_6$-R1) production platforms were generated as described in Examples 1 and 2.
RI Production in the Shake Flasks at the Fed-batch Mode.

The fed-batch shake flask cultivations were performed with the gel based EnBase® system in 1 L baffled Erlenmeyer flasks with 200 mL of MSM medium as earlier described (Šiurkus et al. 2010). Glucose release for substrate limited growth was generated by 12 AGU L$^{-1}$ in the cultivation medium. Product synthesis in the selected expression platforms was induced at OD$_{600}$=5±0.5 (μ≈0.22 h$^{-1}$). Induction was performed by addition of 1 M IPTG to achieve a final concentration of 0.2 mM. The necessary amount of DTT was added as dry powder to the cultivation medium to achieve final concentration of 12 mM. The cytoplasmic and periplasmic expressions were carried for 4 h at 22° C. at a shaking rate of 180 rpm.

Protein analysis. The protein analysis was performed as described in examples 1 and 2.

Figures 8A, 8B:
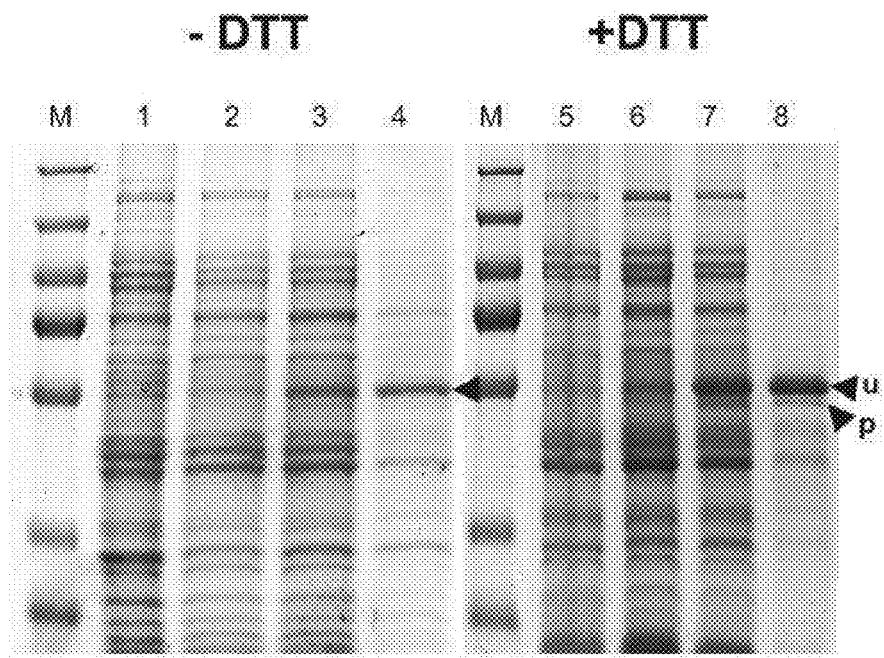
FIGS. 8A, 8B, 8C and 8D show SDS-PAGE images of protein fractions using *E. coli* periplasmic production construct *E. coli* RV308 dsbA$^+$ pCUlac-pelB-RI in the absence (FIG. 8A) or presence (FIG. 8B) of DTT in the medium, and using *E. coli* cytoplasmic production construct RV308 pCUlac His$_6$-RI in the absence (FIG. 8C) and presence (FIG. 8D) of DTT in the medium.
Figures 8C, 8D:
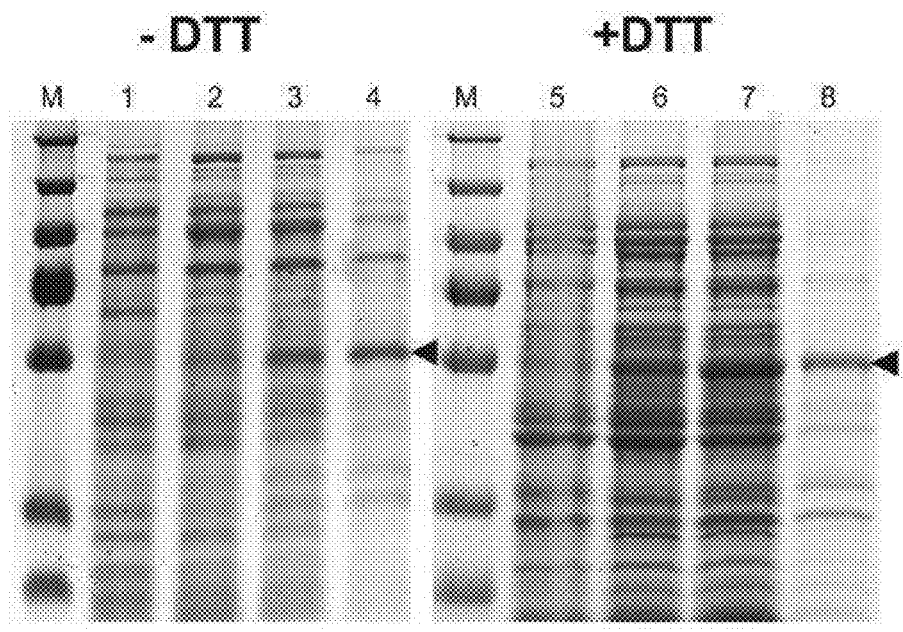

FIGS. 8A-D show 10% SDS-PAGE gel images of protein fractions, normalized to equal amounts, of E. coli periplasmic production construct: E. coli RV308 dsbA$^+$ pCUlac -pelB-RI. FIGS. 8A and 8B represent SDS-PAGE gel images with protein fractions after fed-batch periplasmic RI production with no DTT in the medium (FIG. 8A) and with 12 mM DTT (FIG. 8B). FIGS. 8C-D show 10% SDS-PAGE images of protein fractions of E. coli cytoplasmic production construct: RV308 pCUlac His$_6$-RI. FIGS. 8 C, D represent SDS-PAGE images with protein fractions after fed-batch cytoplasmic RI production at 22° C. with no DTT in the medium (FIG. 8C) and with 12 mM DTT (FIG. 8D). Numbered lanes in the SDS-PAGE gels represent 1—total protein fraction 10 min before RI synthesis induction, lanes 2, 3 and 4—soluble, total and insoluble protein fractions, 4 h after RI synthesis induction. Protein size marker was PageRuler™ Protein Ladder Plus (Fermentas). Arrow ◀ u (FIG. 8A-B) indicates unprocessed RI (53 kDa); arrow ◀ p (FIG. 8A-B) indicates processed RI (50 kDa)arrow; ◀ (FIG. 8C-D) indicates His$_6$-RI (52 kDa). All cultures were initially started at 37° C., induced with 0.2 mM of IPTG and shifted to the respective temperature at the time of RI synthesis induction.

Figure 9:
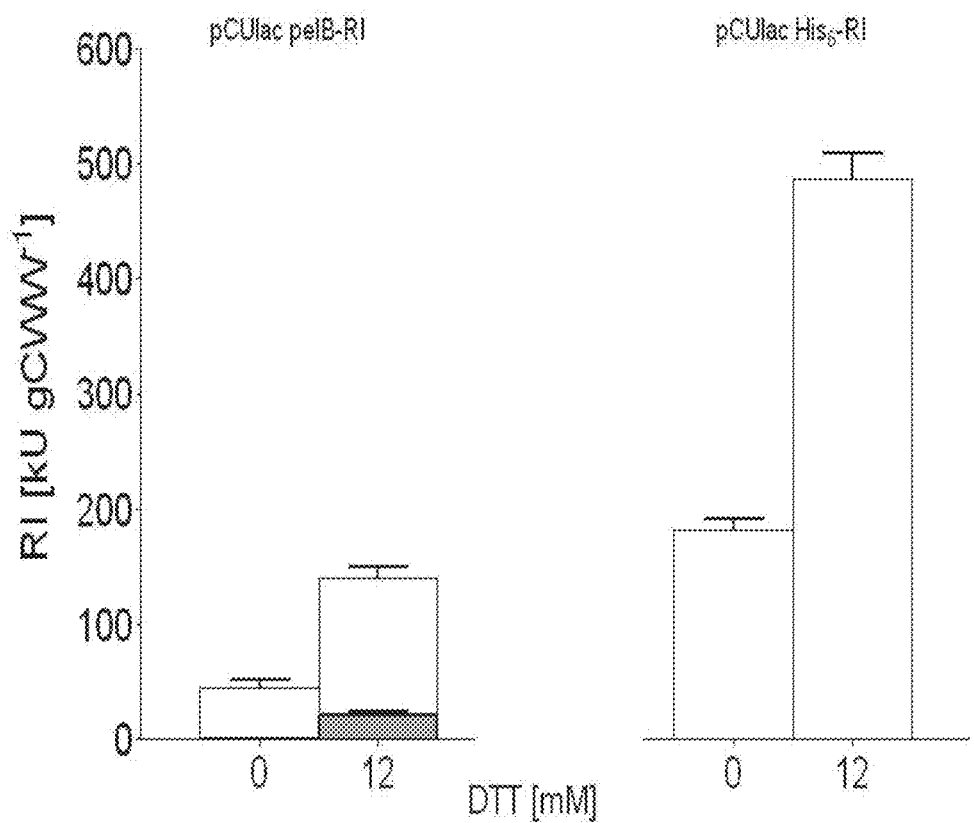
FIG. 9 shows protein activities in total soluble and periplasmic fractions using recombinant production in *E. coli* RV308 pCUlac -pelB-RI and *E. coli* RV308 pCUlac-His$_6$-RI constructs, in the absence or presence of DTT in medium.

FIG. 9 shows RI protein activities in total soluble and periplasmic fractions in kilo units per gram of wet cell weight [kU (gCWW)$^1$] after 4 hours of shake flask fed-batch RI cultivation with recombinant production in E. coli RV308 pCUlac -pelB-RI (left-hand group of bars) and E. coli RV308 pCUlac-His$_6$-RI (right-hand group of bars) constructs, at 22° C., with 0 and 12 mM of DTT in medium, as indicated. Gray-filled bars represent periplasmic RI activity and open white bars represent total RI activity.

Conclusions from Example 3:
(i) Cytoplasmic and periplasmic RI accumulation in soluble protein fraction was significantly improved by supplementation of cultivation medium with DTT in the course of RI fed-batch production.
(ii) The DTT may be utilized for RI folding facilitation when cellular cultivation and recombinant protein production is carried at fed-batch cultivation mode.

EXAMPLE 4

Cytoplasmic and periplasmic production of Ribonuclease inhibitor (RI) (from lungs of Muscardinus avellanarius) with DTT-aided folding in stirred bioreactor.

Preparation of Target Protein Expression Platform.

The cytoplasmic (RV308 pCUlac-His$_6$-RI) and periplasmic (E. coli RV308 pCUlac -pelB-RI) RI production platforms was generated as described in examples 1 and 2.

Bioreactor Process

Batch and fed-batch cultivations were performed in a 10 L working volume Biostat C bioreactor (B. Braun Biotech, Melsungen, Germany), containing 8 L MSM medium, with the following parameters: the pO$_2$ was maintained at 30% by adapting the stirrer rate and automatic regulation of the air flow (from 0 to 30 liters per min), the cultivation temperature before RI periplasmic and cytoplasmic synthesis induction was 37° C. After induction it was downregulated to 22° C. for the whole production process. The pH was controlled at 7.0±0.1 by addition of NH$_4$OH (25%) or H$_3$PO$_4$ (2 M).

The feeding rate was controlled by the Biostat software (version 4.62). The process was monitored by the MFCS/win 2.0 supervisory system. Fed-batch cultivations were started with a volume of 8.0 L of MSM with 15 g L$^{-1}$ of glucose. Exponential feeding profiles were programmed to maintain a specific growth rate of μ≈0.22 h$^{-1}$. The feeding profiles were calculated with following equations:

$$F(t)=F_o\, e^{\mu t}$$

where $F_o$ is the initial feeding rate [L h$^{-1}$], μ is the specific growth rate [h$^{-1}$] to be maintained during feed operation, and t is the time after feed start [h]. The initial feeding rate was calculated from the mass balance on substrate according to $$F_0 = \frac{\mu X_0 V_0}{S_f Y_{x/s}}.$$

Here, $X_0$ and $V_0$ are the cell dry weight (CDW) [g L$^{-1}$] and the culture volume [L] at the time of the feeding start, respectively, $S_f$ [g L$^{-1}$] is the substrate concentration in the feeding solution, and $Y_{x/s}$ is the yield coefficient (g CDW per g of glucose). $Y_{x/s}$ in all calculations, for cytoplasmic and periplasmic expression strains was calculated from batch fermentations as 0.3 g g$^{-1}$.

Before initiation of the fed batch mode cells were cultivated as a batch until OD$_{600}$≈18. The cytoplasmic and periplasmic fed-batch production of RI was induced at the fed-batch cultivation mode at an OD$_{600}$ of 28, the specific growth rate at the time of induction was the same in all cases (μ=0.22 h$^{-1}$). The exponential feed function was continued after induction of the target protein in all fed-batch experiments.

Batch periplasmic and cytoplasmic RI productions were induced at OD$_{600}$≈7 (μ≈0.45 h$^{-1}$). In all bioreactor synthesis experiments 148 mL of 0.65 M DTT solution was added after 2 h of RI induction to achieve a final concentration of 12 mM in the cultivation medium. In the experiments with DTT feeding the same solution was added repeatedly, starting at 2 hours after RI induction by addition of 148 mL of 0.65 M DTT solution and continued by repeated addition of 74 mL 0.65 DTT solution every following 60 min. At the first DTT addition point the air flow was decreased from 30 to 2-4 L min$^{-1}$ and the stirrer was manually regulated to maintain 0% of oxygen concentration in the cultivation medium. In all cases the target protein synthesis continued for another 3 hours.

Protein analysis. The protein analysis was performed as described in Examples 1 and 2.

Figure 10:
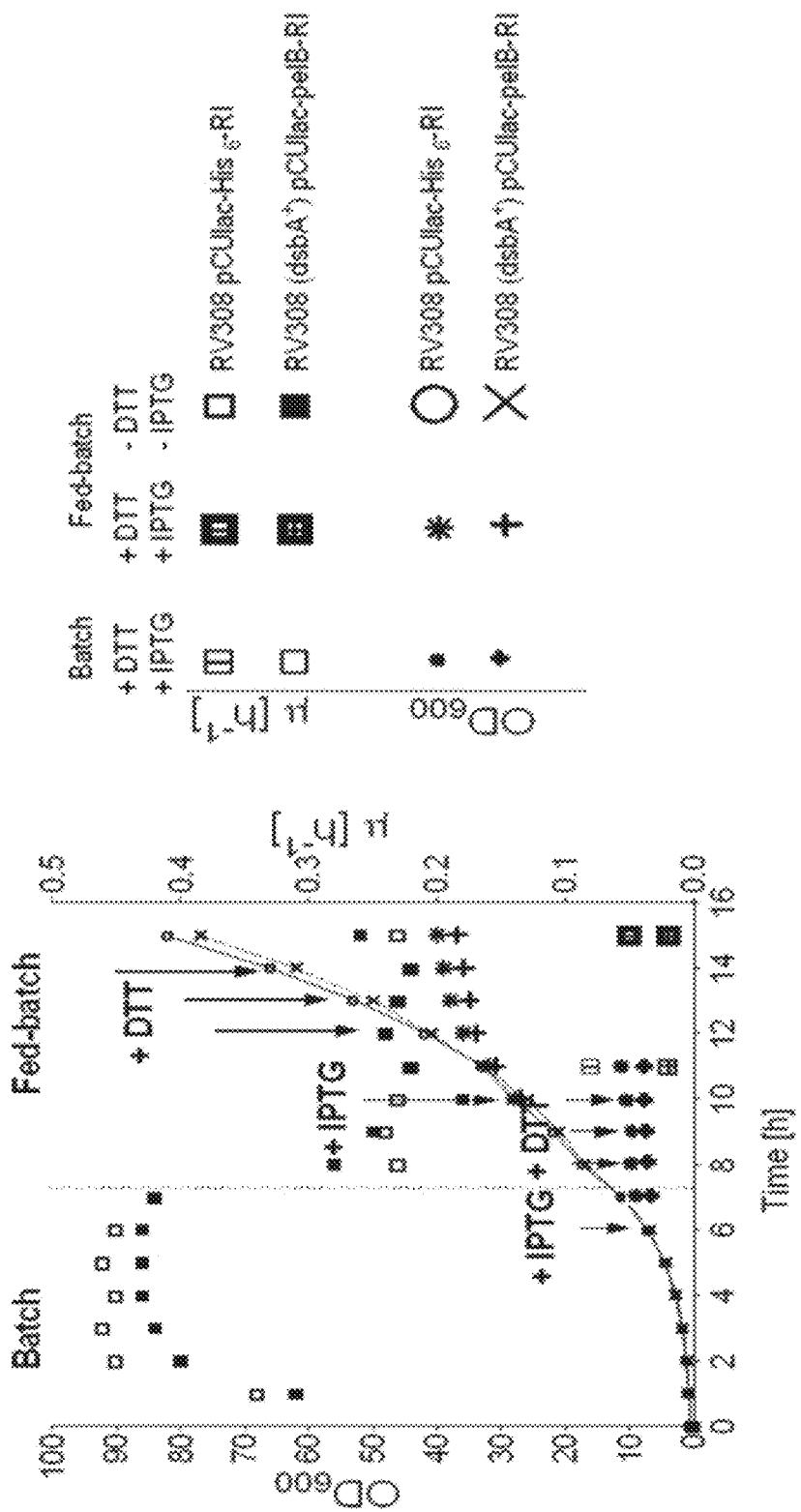
FIG. 10 shows exemplary growth curves of *E. coli E. coli* RV308 pCUlac-pelB-RI and *E. coli* RV308 pCUlac-His$_6$-RI constructs without (control) and with protein production in a batch and a fed-batch process.

FIG. 10 shows exemplary growth curves of E. coli E. coli RV308 pCUlac-pelB-R1 and E. coli RV308 pCUlac-His$_6$-RI constructs without (control) and with RI protein production in a batch and a fed-batch process with exponential glucose feeding in a 10 L bioreactor with a starting volume of 8 L glucose-MSM and an initial glucose concentration of 15 g L$^{-1}$. The growth temperature was maintained at 37° C. and shifted to 22° C. after RI induction. The medium was supplemented with 12 mM of DTT starting from 2 hours after RI induction. The fed-batch operation was started at $OD_{600}\approx18$. Induction RI production was induced by 0.2 mM IPTG 1.5 to 2 h after arabinose addition at $OD_{600}\approx28$ ($\mu=0.22\pm0.02$ $h^{-1}$) and continued for 5 hours at 22° C. Batch cultivation: RI synthesis was induced by 0.2 mM IPTG at $OD_{600}=7.0$ ($\mu=0.45\pm0.02$ $h^{-1}$). RI production was carried on for 5 hours at 22° C. in all cases.

FIGS. 11A-11B show RI activities in normalized per cell amount crude extracts E. coli of RV308 pCUlac-His$_6$-RI (FIG. 11A) and RV308 pCUlac pelB-RI (FIG. 11B) constructs, in kilo units per gram of wet cell weight [kU (gCWW)$^{-1}$] from samples of batch and fed-batch bioreactor cultivations without and with addition of DTT. Activities from soluble protein fraction—total (open/white bars) and periplasmic (gray bars) are shown. Black box indicates DTT feeding and black triangle (▼) indicates DTT single addition. Induction of RI synthesis was performed at the indicated $OD_{600}$ values of $\approx28$ for the fed-batch production and $\approx6$ for batch production, respectively. The data are derived from three activity assays.

Conclusions from Example 4:
(i) Process scalability: DTT based RI folding in vivo approach was also applicable in the stirred bioreactor, process was scalable.
(ii) The DTT mediated RI folding during bioreactor production course was applicable under the batch and fed-batch cultivation modes at the high cell density range.
(iii) Repeated DTT addition during RI production course in the stirred bioreactor gave maximum positive effect on periplasmic and cytoplasmic RI folding in E. coli cells.
(iv) Microaerobic conditions (during RI production course with medium supplemented with DTT) are necessary to maximize positive DTT effect on RI folding.

EXAMPLE 5

The DTT effect on RI activity and soluble accumulation in T7 expression system with increased synthesis levels of molecular chaperones GroEL-GroES when RI production is carried in stirred bioreactor.

Expression Strain Preparation

E. coli strain ER2566 (DE3) was transformed with plasmid pET21b-RI encoding RI and plated on LB agar with ampicillin (100 µg mL$^{-1}$). The expression strain E. coli ER2566 pET21b-RI was transformed with the chaperone genes GroEL-GroES carrying expression vector pGro7 (Takara Bio Inc.). Transformants harboring both plasmids were selected by plating onto LB agar containing ampicillin (100 µg mL$^{-1}$) and chloramphenicol (30 µg mL$^{-1}$). Both transformations were based on the calcium temperature shock method. The glycerol cell stocks were produced after 8 h of transformant cell cultures cultivation in liquid LB medium, containing required antibiotics at 37° C., 220 rpm. The 50% sterile glycerol solution was used to produce 25% glycerol stock cell stocks which were aliquoted into Eppendorf tubes and stored at –70° C.

Bioreactor Processes

Batch and Fed-batch cultivations were performed in 10 L working volume Biostat C bioreactor (B. Braun Biotech, Melsungen, Germany) in the 8 liters of final MSM medium (Siurkus et al. 2010). The initial fermentation parameters were maintained as follows: the pO$_2$—at 30% by adapting the stirrer rate and automatic regulation of the air flow (from 0 to 30 liters per min), pH was controlled at 7.0±0.1 by addition of NH$_4$OH (25%) or H$_3$PO$_4$ (2 M). During all bioreactor processes the growth temperature before and after GroEL\ES synthesis induction was maintained at 37° C. The temperature in all processes was down-regulated from 37° C. to 22° C. only at RI synthesis induction point. The DTT feeding was started 2 hours after RI synthesis induction, by initial supplementation of MSM medium with 0.65 M DTT solution to achieve final DTT concentration of 12 mM. The necessary amount of 0.65 M DTT concentrate was added at two following hours to achieve $\approx6$ mM final DTT concentration in the fermentation medium.

At the DTT addition point the air flow was reduced from 30 to 3-4 L min$^{-1}$ and stirring was manually regulated to maintain the oxygen concentration at 0% in the fermentation medium during cell cultivation in the presence of DTT. The feeding of the fed-batch fermentations was controlled by the Biostat software (version 4.62). All fermentation processes were monitored by the MFCS/win 2.0 supervisory system. Exponential feeding profiles were programmed to maintain a specific growth rate of $\mu\approx0.22$ $h^{-1}$ (Siurkus et al. 2010).

Fed-batch cultivations were started with a volume of 8.0 L of MSM containing 8 and 15 g L$^{-1}$ of glucose, respectively. The fed-batch mode cultivation was started after the initial batch cultivation at $OD_{600}\approx9.5$ and $OD_{600}\approx18$, respectively. The biosynthesis of the chaperones GroEL-GroES was induced 1 h before RI induction at $OD_{600}\approx12.5$-14, and $OD_{600}\approx24$-26 in both cases respectively at $\mu\approx0.22$ $h^{-1}$ at the substrate limited growth. The RI fed-batch production was induced at $OD_{600}\approx18$ and $OD_{600}\approx38$ in both cases at $\mu=0.22\pm0.02$ h 1 and continued for 5 hours at 22° C. The batch fermentations were performed in 8 L of MSM medium containing 15 g L$^{-1}$ of glucose. The induction of GroEL-GroES at the batch cultivation mode was performed at $OD_{600}$ 3.0. RI synthesis induction was carried after 1 hour at $OD_{600}$ of 6.0. The chaperon and RI synthesis inductions were performed at specific growth rate µ of $\approx0.5$ $h^{-1}$ and carried for 5 hours at 22° C.

Protein Analysis

Cell samples harvested from flask and bioreactor cultivations were resuspended in lysis buffer with biomass/buffer ratio: 1 g of biomass with 10 mL of lysis buffer (50 mM Tris-H3PO4 pH 8.0, 0.1% Triton X-100, 2 mM EDTA, 1 mM PMSF, 12 mM DTT, 10% propyleneglycol and 0.1 mg mL-1 lysozyme). After 30 min of lysis at +4° C. the biomass was disrupted by sonication for 60 sec (Vibra cell™, Sonic and Materials Inc., 6 mm diameter probe tip) at 4° C. Soluble and insoluble protein fractions were separated by centrifugation for 30 min, 14000 rpm, 4° C. Total protein fraction is represented by cellular debris suspension (crude extract) before centrifugation. After centrifugation the insoluble protein pellet was additionally washed and resuspended in original volume of lysis buffer without lysozyme.

Samples for SDS-PAGE separation were prepared from the following components: 20 µL of protein sample (total soluble, insoluble, protein suspensions), 25 µL of 4×SDS-PAGE loading buffer (Fermentas), 5 µL of 20×DTT (Fermentas) and 50 µL of deionized to obtain a final sample volume of 100 µL. Samples were heated for 15 min at 95° C. Ten µL of sample was applied to each lane of a 10% SDS-PAGE gel.

The amounts in mg of target RI were determined from scanned SDS-PAGE gel images by treatment of images with TotalLab software. Gels with separated sample proteins for TotalLab quantifications were produced with internal BSA standards (3 concentration points).

The amount of active RI in the protein fraction was determined by activity assay described by Blackburn et. al, 1977, 1978.

Figure 12A:
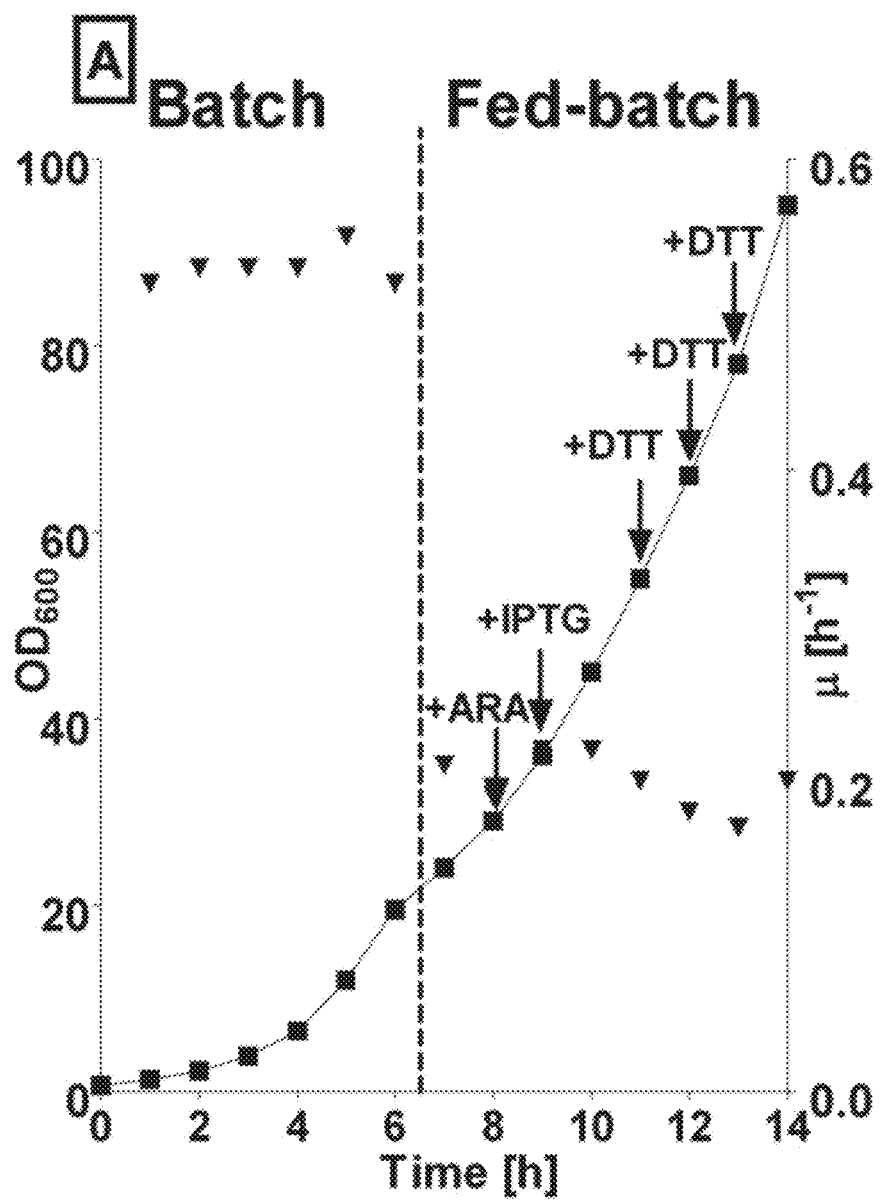
FIGS. 12A and 12B show exemplary growth curves of *E. coli* ER2566 pET21bRI pGro7 with protein production in a fed-batch process (FIG. 12A) and the fed-batch conditions (FIG. 12B).
Figure 12B:
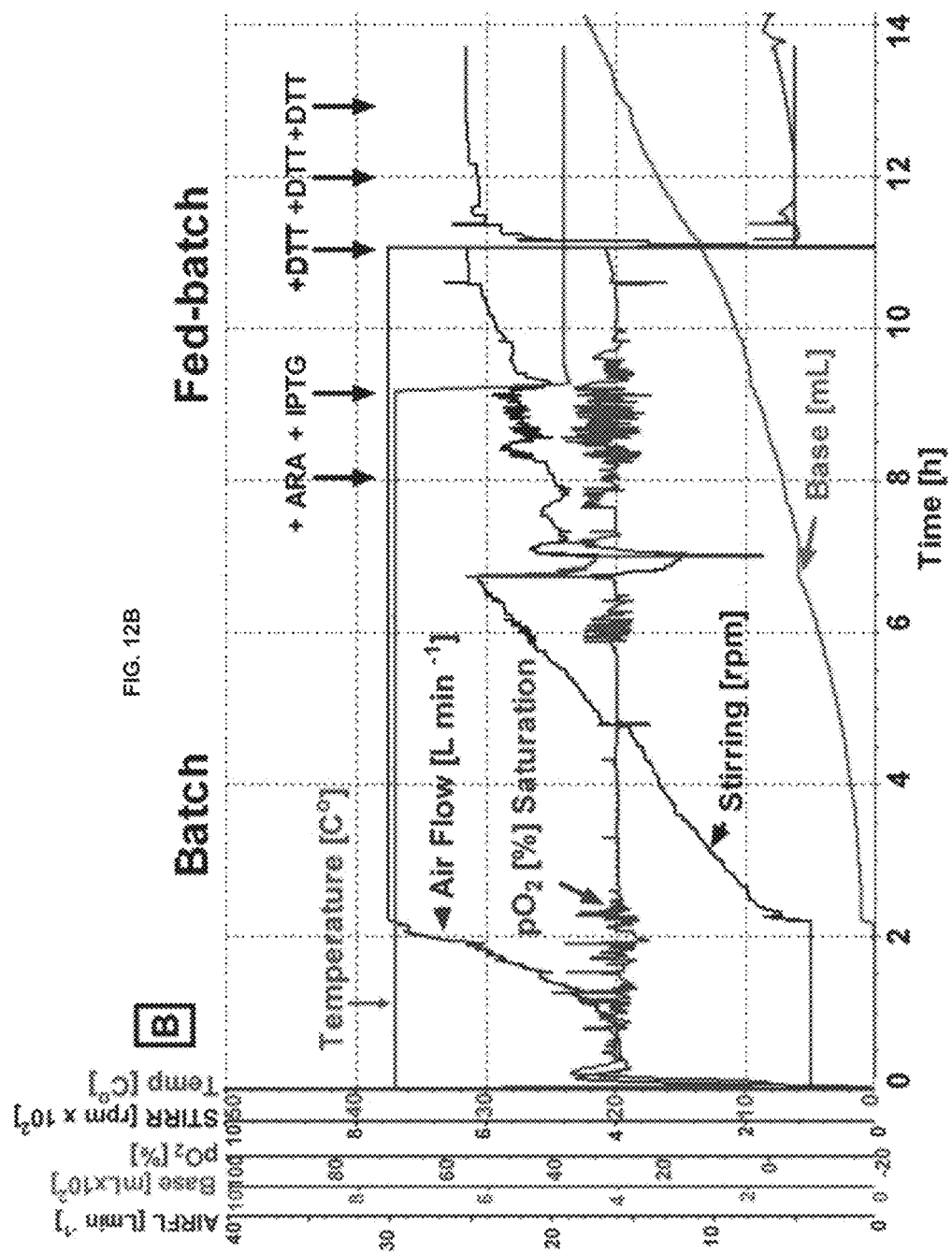

FIG. 12A shows exemplary growth curves of E. coli ER2566 pET21bRI pGro7 with RI protein production in a fed-batch process with exponential glucose feeding in a 10 L bioreactor with a starting volume of 8 L glucose-MSM and an initial glucose concentration of 15 g $L^{-1}$, where black-filled squares represent $OD_{600}$ data and back-filled triangles represent μ [$h^{-1}$]. FIG. 12B shows that the growth temperature was maintained at 37° C. and shifted to 22° C. after RI induction; the medium was supplemented with 12 mM of DTT starting from 2 hours after RI induction and each following production hour. The fed-batch operation was started at $OD_{600}$≈18. Induction of GroEL/ES was performed with 0.4 g $L^{-1}$ of arabinose $OD_{600}$≈24 (μ≈0.22 $h^{-1}$). RI production was induced by 0.2 mM IPTG 1.5 to 2 h after arabinose addition at $OD_{600}$≈38 (μ≈0.22±0.02 $h^{-1}$) and continued for 5 hours at 22° C.

Figure 13A:
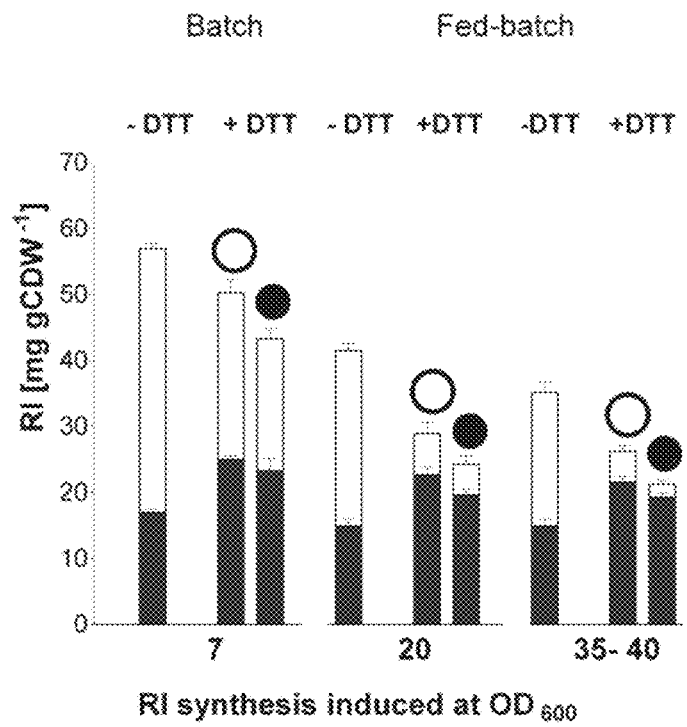
FIGS. 13A and 13B show protein amounts and activities from samples of batch and fed-batch bioreactor cultivations in the absence or presence of DTT.
Figure 13B:
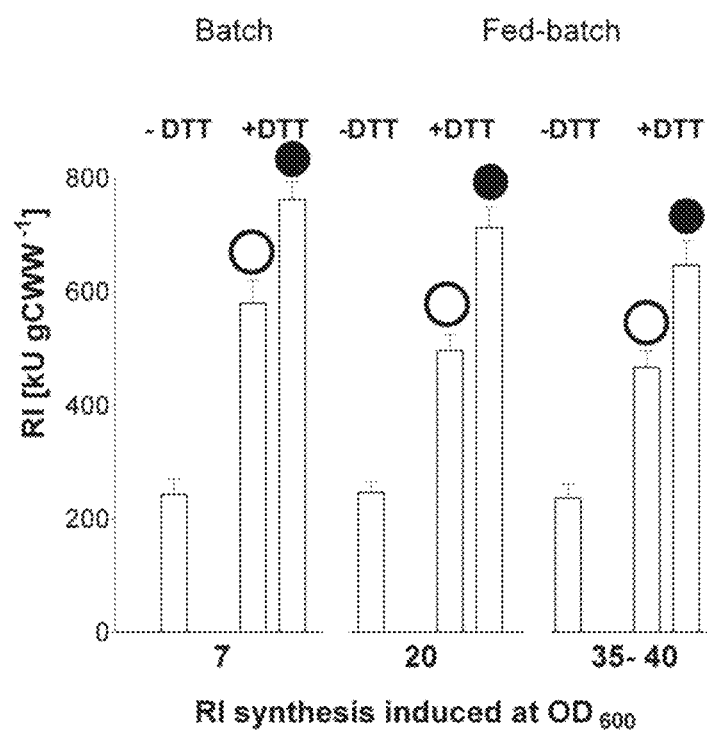

FIGS. 13A-B show RI amounts and activities normalized per cell amount from samples of batch and fed-batch bioreactor cultivations without and with addition of DTT which was either added once (open circles) or repeatedly (one pulse per hour, filled circles). The first addition of DTT was performed always two hour after induction of RI. FIG. 13A: total (white bars) and soluble (black bars) RI amount as mg per g cell dry weight [mg(g CDW)$^{-1}$]. FIG. 13B: RI activities in normalized crude extracts, in kilo units per gram of wet cell weight [kU (gCWW)$^{-1}$]. Induction of RI synthesis was performed at the indicated $OD_{600}$ values of 7 for the batch production and 20 or 35-40 for fed-batch production. The data are derived from 3 independent assays.

Figure 14A:
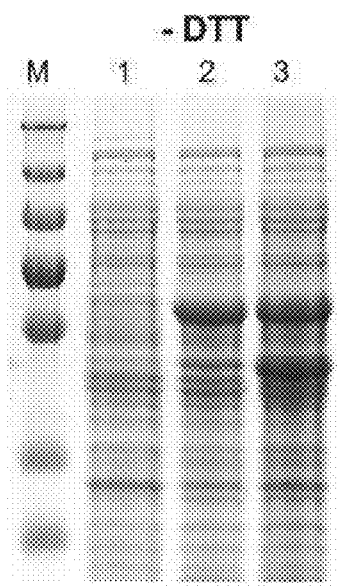
FIGS. 14A, 14B, 14C and 14D show SDS-PAGE images of protein fractions using production construct *E. coli* ER2566/pET21bRI/pGro7 after batch protein production in the absence (FIG. 14A) and presence (FIG. 14B) of DTT, and using production construct *E. coli* ER2566/pET21bRI/pGro7 after fed-batch bioreactor production in the absence (FIG. 14C) and presence (FIG. 14D) of DTT.
Figure 14B:
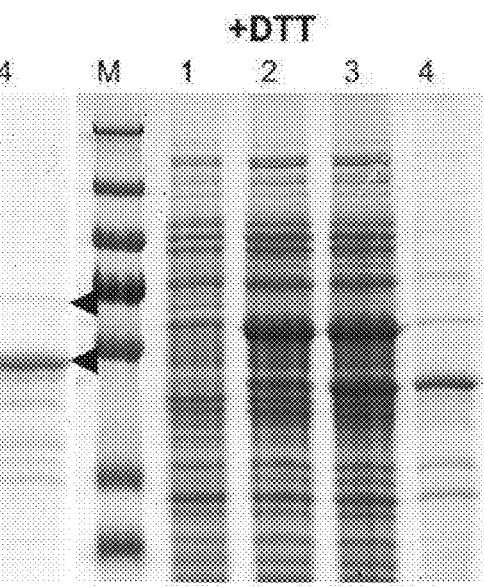
Figure 14C:
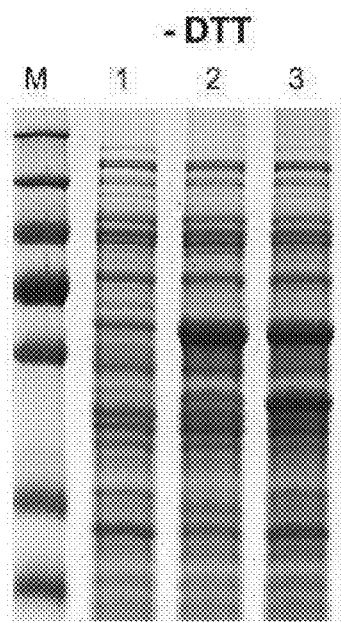
Figure 14D:
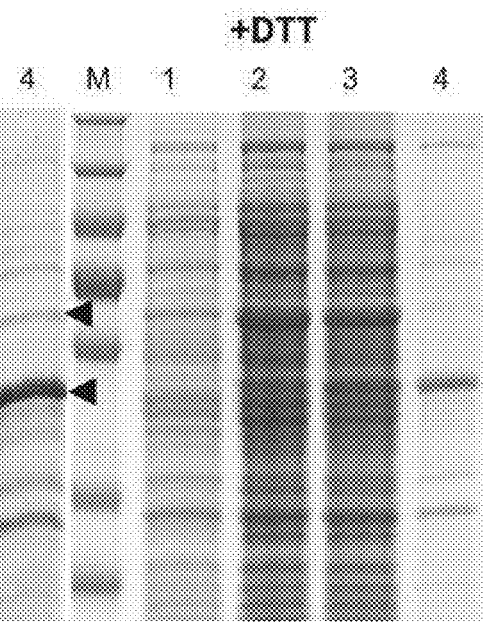

FIGS. 14A-D show 10% SDS-PAGE gel images of protein fractions, normalized to equal amounts, of production construct: E. coli ER2566/pET21bRI/pGro7 after RI batch and fed-batch bioreactor productions. FIGS. 14A and B represent SDS-PAGE images with protein fractions after batch RI production with no DTT in the medium (FIG. 14A) and with a single addition of 12 mM DTT (FIG. 14B). FIGS. 14C and D represent SDS-PAGE gel images with protein fractions after batch RI fed-batch production with no DTT in the medium (FIG. 14C) and with a single addition of 12 mM DTT (FIG. 14D). Numbered SDS-PAGE gel lanes represent: 1—total protein fraction 10 min before RI and GroE/ES synthesis induction, 2—soluble protein fraction, 3—total protein fraction and 4—insoluble protein fraction 4 h after RI synthesis induction. Protein size marker was PageRuler™ Protein Ladder Plus (Fermentas).

Conclusions from Example 5
(i) For RI cytoplasmic folding DTT utilization could be combined with utilization of folding aiding molecular chaperones (DTT was compatible with utilization of molecular chaperones or other biological factors aiding folding).
(ii) Combined (DTT and chaperone mediated) approach for RI folding was applicable both in batch and fed-batch bioreactor production processes in very high cell density ranges.

EXAMPLE 6

DTT-mediated improvement of soluble accumulation of fusion protein RpoB-lysC, (200 kDa) during production in the batch shake flasks (RpoB—E. coli RNA polymerase, β subunit; lysC—E. coli aspartate kinase III).
RpoB-lysC Fusion Protein Contains 12 Cysteines.
Production Strain Preparation.
E. coli strain JM109 was transformed with plasmid pASK-RpoB-lysC carrying resistance for ampicillin and plated on LB agar with ampicillin (100 μg $mL^{-1}$). Transformation was based on the calcium temperature shock method. The glycerol cell stocks were produced after 8 h of transformed cultures cultivation in liquid LB medium containing required antibiotics at 37° C., 220 rpm. The 50% sterile glycerol solution was used to produce 25% glycerol cell stocks which were aliquoted into Eppendorf tubes and stored at −70° C.

RpoB-lysC Batch Production in the Shake Flasks.
The inoculums for batch protein production in the shake flasks were prepared by overnight batch cultivation of the selected clones in 500 mL shake flasks with 50 ml of LB medium. For protein production 5% of the corresponding inoculum culture was transferred to fresh LB medium to the final volume of 500 mL in 2 L baffled Erlenmeyer shake flasks. Cultures were cultivated at 37° C. and 180 rpm until they reached the induction point corresponding to a cell density of $OD_{600}$=0.7±0.05 (μ≈0.5 $h^{-1}$). Induction was performed by addition of 2 mg/mL anhidro tetracycline (AHT) to a final concentration of 0.2 mg/L. DTT was added to the cultivation medium at the RpoB-lysC synthesis induction point as dry powder to achieve the needed concentration of 15 mM. Cytoplasmic expression was carried for 4 h at 30° C. at a shaking rate of 180 rpm.

Protein Analysis
Cell samples harvested from flask or cultivations were resuspended in lysis buffer with the following biomass to buffer ratio: 1 g of biomass with 10 mL of lysis buffer (50 mM Tris-$H_3PO_4$ pH 8.0, 0.1% Triton X-100, 2 mM EDTA, 1 mM PMSF, 1 mM DTT and 0.1 mg $mL^{-1}$ lysozyme). After 30 min of lysis at +4° C. the biomass was disrupted by sonication for 60 sec (Vibra cell™, Sonic and Materials Inc., 6 mm diameter probe tip) at 4° C. Soluble and insoluble protein fractions were separated by centrifugation for 30 min, 14000 rpm, at 4° C. The total protein fraction was represented by cellular debris suspension (crude extract) before centrifugation. After centrifugation the insoluble protein pellet was additionally washed and resuspended in the original volume of lysis buffer without lysozyme.

Samples for SDS-PAGE separation were prepared as follows: 20 μL of protein sample (total soluble, insoluble, protein suspensions), 25 μL of 4×SDS-PAGE loading buffer (Fermentas), 5 μL of 20×DTT (Fermentas) and 50 μL of deionized water to obtain a final sample volume of 100 μL. Samples were heated for 15 min at 95° C. 10 μL of sample was applied to each lane of a 8% SDS-PAGE gel.

Differences in the amounts of RpoB-lysC in soluble fractions after test productions with and without DTT were evaluated from scanned SDS-PAGE gel images by image treatment with TotalLab software.

Figures 15A, 15B:
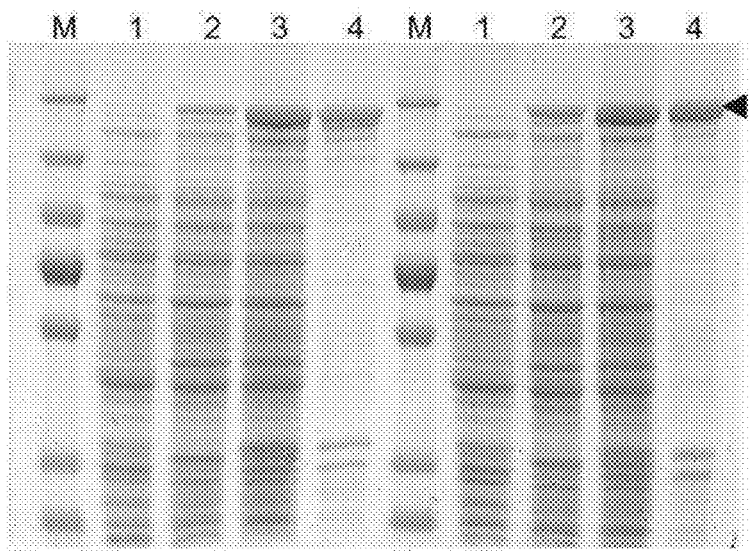
FIGS. 15A and 15B show SDS-PAGE images of protein fractions using production construct JM109 pASK RpoB-LysC in the absence (FIG. 15A) and presence (FIG. 15B) of DTT.

FIGS. 15A-B show 8% SDS-PAGE gel images of normalized to equal amounts protein fractions of production construct: JM109 pASK RpoB-LysC after 4 hours of batch RpoB-LysC production at 30° C. Panels are representing SDS-PAGE images with protein fractions after RpoB-LysC production with no DTT in the medium (FIG. 15A) and with 15 mM DTT (FIG. 15B), respectively. Numbered SDS-PAGE gel lanes represents: 1—total protein fraction 10 min before induction, 2—soluble protein fraction, 3—total protein fraction and 4—insoluble protein fraction (all 4 h after induction). Protein size marker was PageRuler™ Protein Ladder Plus (Fermentas). Arrow ◄ (FIG. 15A-B) indicates RpoB-LysC fusion protein. All cultures were initially started at 37° C., induced with 0.2 mg/L of AHT and shifted to the respective temperature at the time of RpoB-LysC synthesis induction.

Conclusions from Example 6:
Accumulation of nonfunctional fusion protein RpoB-LysC (prokaryotic origin) in E. coli cytoplasmic space was reduced by supplementation of the cultivation medium with DTT in the course of recombinant protein production.

EXAMPLE 7

DTT-mediated improvement of soluble accumulation of fusion protein Trx-EK, (46 kDa) during production in the batch shake flasks (TrxA—*E. coli* thioredoxin A; EK Bovine enterokinase light chain).
Trx-EK Fusion Protein Contains 11 Cysteines.
Production Strain Preparation.

The strain BL21 was transformed with plasmid pET32a Trx-EK carrying resistance for ampicillin and plated on LB agar with ampicillin (100 μg mL$^{-1}$). Transformation was based on the calcium temperature shock method. The glycerol cell stocks were produced after 8 h of transformed cultures cultivation in liquid LB medium, containing required antibiotics at 37° C., 220 rpm. The 50% sterile glycerol solution was used to produce 25% glycerol stock cell stocks which were aliquoted in Eppendorf tubes and stored at −70° C.
Trx-EK Production in the Shake Flasks.

Inoculums for batch protein production in shake flasks were prepared by overnight batch cultivation of selected clones in 500 mL shake flasks with 50 ml of LB medium. For protein production 5% of the corresponding inoculum culture was transferred to fresh LB medium to the final volume of 500 mL in 2 L baffled Erlenmeyer shake flasks. Cultures were cultivated at 37° C. and 180 rpm until they reached the induction point, corresponding to a cell density of $OD_{600}=0.7\pm0.05$ ($\mu\approx0.5$ h$^{-1}$). Induction was performed by addition of 1 M IPTG to the final concentration of 0.1 mM. The DTT was added to the cultivation medium at the Trx-EK synthesis induction point as dry powder to achieve needed concentration of 15 mM. Cytoplasmic expression was carried for 4 h at 22° C. at a shaking rate of 180 rpm.
Protein Analysis Cell samples harvested from flask or cultivations were resuspended in lysis buffer with the following biomass to buffer ratio: 1 g of biomass with 10 mL of lysis buffer (50 mM Tris-H$_3$PO$_4$ pH 8.0, 0.1% Triton X-100, 2 mM EDTA, 1 mM PMSF, 2 mM DTT and 0.1 mg mL$^{-1}$ lysozyme). After 30 min of lysis at +4° C. the biomass was disrupted by sonication for 60 sec (Vibra cell™, Sonic and Materials Inc., 6 mm diameter probe tip) at 4° C. Soluble and insoluble protein fractions were separated by centrifugation for 30 min, 14000 rpm, 4° C. Total protein fraction is represented by cellular debris suspension (crude extract) before centrifugation. After centrifugation the insoluble protein pellet was additionally washed and resuspended in the original volume of lysis buffer without lysozyme.

Samples for SDS-PAGE separation were prepared as follows: 20 μL of protein sample (total soluble, insoluble, protein suspensions), 25 μL of 4×SDS-PAGE loading buffer (Fermentas), 5 μL of 20×DTT (Fermentas) and 50 μL of deionized water to obtain a final sample volume of 100 μL. Samples were heated for 15 min at 95° C. 10 μL of sample was applied to each lane of a 10% SDS-PAGE gel.

Differences in the amounts of Trx-EK in soluble fractions after test productions with and without DTT in the medium were evaluated from scanned SDS-PAGE gel images by image treatment with TotalLab software.

Figures 16A, 16B:
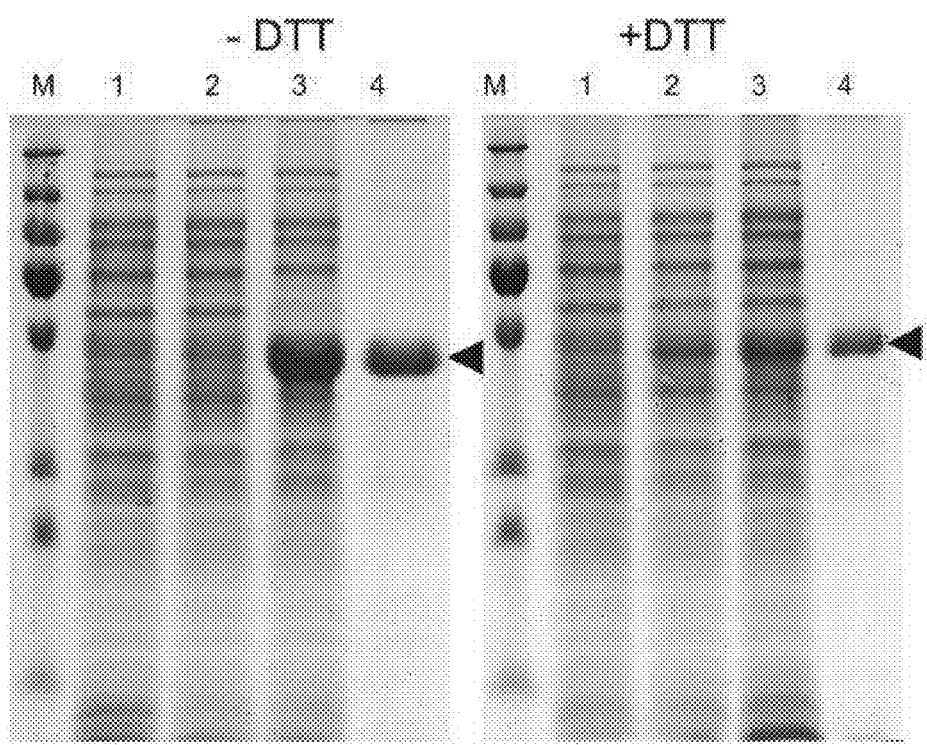
FIGS. 16A and 16B show SDS-PAGE images of protein fractions using production construct *E. coli* BL21 pET32a-Trx-EK in the absence (FIG. 16A) and presence (FIG. 16B) of DTT.

FIGS. 16A-B show 10% SDS-PAGE gel images of normalized to equal amounts protein fractions of production construct *E. coli* BL21 pET32a-Trx-EK after 4 hours of batch Trx-EK production at 22° C. FIG. 16A represents SDS-PAGE gel image with protein fractions after Trx-EK production with no DTT in the medium and FIG. 16B with 15 mM DTT respectively. Numbered lanes in the SDS-PAGE gels represents: 1—total protein fraction 10 min before Trx-EK synthesis induction. Numbered SDS-PAGE gel lanes represents: 1—total protein fraction 10 min before induction, 2—soluble protein fraction, 3—total protein fraction and 4—insoluble protein fraction 4 h after Trx-EK synthesis induction. Protein size marker was PageRuler™ Protein Ladder Plus (Fermentas). Arrow ◀ (FIG. 16A-B) indicates Trx-EK protein. All cultures were initially started at 37° C., induced with 0.1 mM of IPTG and shifted to the respective temperature at the time of Trx-EK synthesis induction.
Conclusions from Example 7:

Accumulation of eukaryotic protein—EK fused with prokaryotic protein Trx was improved by supplementation of the cultivation medium with DTT during the course of recombinant protein production.

EXAMPLE 8

DTT mediated improvement of soluble accumulation and active DnaseI yield. Bovine pancreas DnaseI (31 kDa) contains 4 cysteines.
Production Strain Preparation.

*E. coli* strain HM174 was transformed with plasmid pET21b-DnaseI encoding recombinant DnaseI and plated on LB agar with ampicillin (100 μg mL$^{-1}$) for transformant selection. Transformation was based on the calcium temperature shock method.
DnaseI Production in the Batch Shake Flasks.

The inoculums for batch protein production in the shake flasks were prepared by overnight batch cultivation of the selected clones in 500 mL shake flasks with 50 ml of LB medium. For protein production 5% of the corresponding inoculum culture was transferred to fresh semi synthetic medium with following composition: 4.1 g/L KH$_2$PO$_4$, 3.2 g/L K$_2$HPO$_4$ (pH 7.0 adjusted), 5 g/L NaCl, 5 g/L yeast extract, 10 g/L tryptone and 5 g/L glycerol. The final medium volume in 2 L baffled Erlenmeyer shake flasks was 500 mL. Cultures were cultivated at 37° C. and 180 rpm until they reached the induction point corresponding to cell density of $OD_{600}=0.7\pm0.05$ ($\mu\approx0.3$ h$^{-1}$). Induction was performed by addition of 1 M IPTG to the final concentration of 0.1 mM. DTT was added to the cultivation medium at the DnaseI synthesis induction point as dry powder to achieve the final concentration of 15 mM. Cytoplasmic expressions were carried for 4 h at 37° C. at the shaking rate of 180 rpm.
Protein Analysis Cell samples harvested from flasks or cultivations were resuspended in lysis buffer with the following biomass to buffer ratio: 1 g of biomass with 10 mL of lysis buffer (50 mM Tris-H$_3$PO$_4$ pH 8.0, 0.1% Triton X-100, 1 mM CaCl$_2$ and 0.1 mg mL$^{-1}$ lysozyme). After 30 min of lysis at +4° C. the biomass was disrupted by sonication for 60 sec (Vibra cell™, Sonic and Materials Inc., 6 mm diameter probe tip) at 4° C. Soluble and insoluble protein fractions were separated by centrifugation for 30 min, 14000 rpm, 4° C. Total protein fraction is represented by cellular debris suspension (crude extract) before centrifugation.

For DnaseI activity assay cell crude extracts after recombinant production were diluted in lysis buffer (without lysozyme) as follows: 50, 250, 1000, 2500, 5000, 10000, 15000, 20000 and 25000 times. The commercial DnaseI (Fermentas, catalog number #EN0521) was diluted in lysis buffer as follows: 50, 250, 500, 1000, 1500, 2000, 2500, 3500 and 5000 times. The reaction was performed in 30 μL mixture with composition of: 1 μg of pUC57 DNA, DnaseI reaction buffer (100 mM Tris-HCl (pH 7.5 at 25° C.) 25 mM $MgCl_2$, $CaCl_2$ 1 mM), 5 units (0.1 μL) RnaseA (Fermentas #EN0531), 1 μL of diluted sample (or commercial enzyme) and required amount of nuclease free water. The reaction was performed for 10 minutes at 37° C. and stopped by heating at 70° C. for 10 minutes, after supplementation with SDS containing loading dye (Fermentas #R1151) and $Na_2EDTA$ (final concentration of 5 mM). Finally, 15 μL of inactivated reaction mixture was applied on 1% agarose gel for DNA electrophoresis.

Samples for SDS-PAGE separation were prepared as follows: 20 μL of protein sample (total soluble, insoluble, protein suspensions), 25 μL of 4×SDS-PAGE loading buffer (Fermentas), 5 μL of 20×DTT (Fermentas) and 50 μL of deionised water to obtain a final sample volume of 100 μL. Samples were heated for 15 min at 95° C. Ten μL of sample was applied to each lane of a 10% SDS-PAGE gel.

Differences in amounts of DnaseI in soluble fractions after test productions with and without DTT in the medium were evaluated from scanned SDS-PAGE gel images by image treatment with TotalLab software.

Figures 17A, 17B:
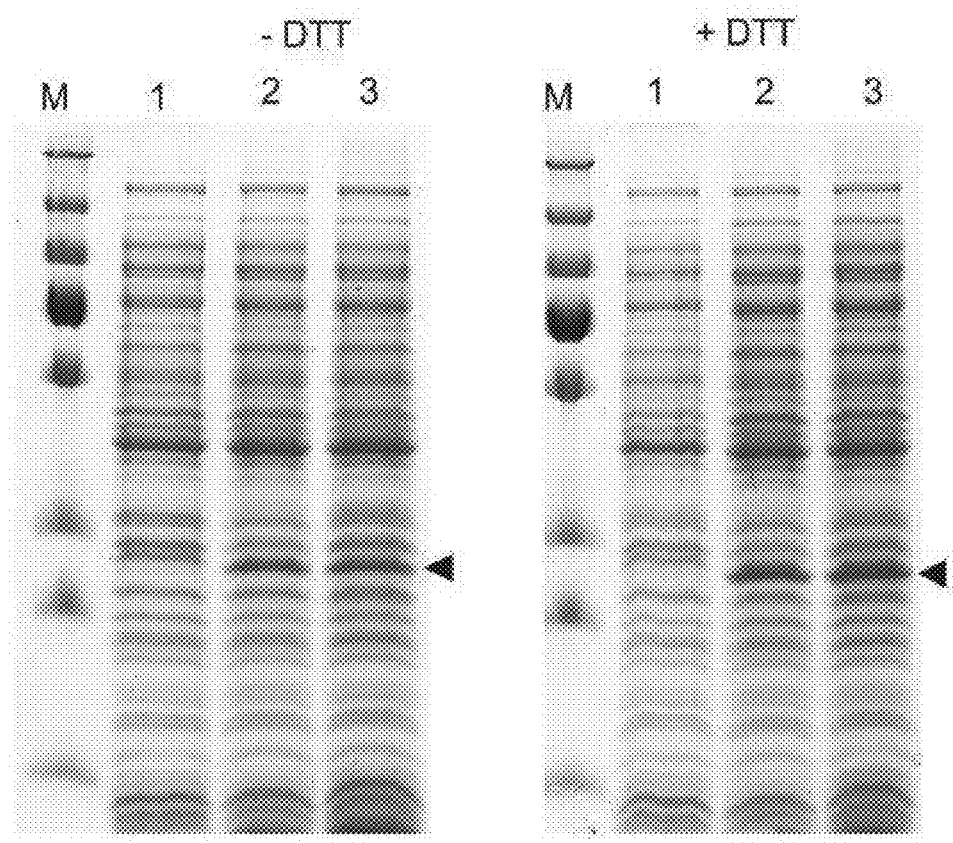
FIGS. 17A and 17B show SDS-PAGE images of protein fractions using *E. coli* production construct HMS174 pET21-DnaseI in the absence (FIG. 17A) and presence (FIG. 17B) of DTT.

FIGS. 17A-B show SDS-PAGE images of normalized to equal amounts protein fractions of *E. coli* production construct HM5174 pET21-DnaseI after 4 hours of batch DnaseI production at 37° C. FIG. 17A represents 10% SDS-PAGE gel image with protein fractions after DnaseI production with no DTT in the medium and FIG. 17B with 15 mM DTT. Numbered lanes in the SDS-PAGE gels represents: 1—total protein fraction 10 min before DnaseI synthesis induction. Numbered SDS-PAGE gel lanes represents: 1—total protein fraction 10 min before induction, 2—soluble protein fraction and 3—total protein fraction 4 h after DnaseI synthesis induction. Protein size marker was PageRuler™ Protein Ladder Plus (Fermentas). Arrow ◄ (FIG. 16A-B) indicates DnaseI. All cultures were initially started at 37° C., induced with 0.1 mM of IPTG the same temperature was maintained for the remaining recombinant production course.

FIGS. 18A-D show images of 1% agarose gel after DNA electrophoresis, with samples generated after soluble protein extracts (FIGS. A, C) and commercial DnaseI (FIGS. B, D) incubation with 1 μg of pUC57 DNA in DnaseI reaction mixture. In FIGS. A and C, gel lanes are representing samples from reaction mixtures with different dilutions (lane 2: ×50, lane 3: ×250, lane 4: ×1000, lane 5: ×2500, lane 6: ×5000, lane 7: ×10000, lane 8: ×15000, lane 9: ×20000 and lane 10: ×25000 times) of soluble protein fraction after recombinant production of DnaseI in HMS174 pET21 DnaseI construct at 37° C. in the cultivation medium without DTT (FIG. 18A) and with 15 mM DTT (FIG. 18C). In FIG. 18B, D gel lanes are representing samples from reaction mixtures with different dilutions (lane 2: ×50, lane 3: ×250, lane 4: ×500, lane 5: ×1000, lane 6: ×1500, lane 7: ×2000, lane 8: ×2500, lane 9: ×3500 and lane 10: ×5000 times) of commercial Dnase I. In all gels, lane 1 is representing pUC57 DNA without treatment with DnaseI samples.

Conclusions from Example 8:
(i) Soluble accumulation of functional DnaseI (eukaryotic origin) in *E. coli* cytoplasmic space was improved by supplementation of cultivation medium with DTT during course of recombinant protein production.
(ii) Activity (folding) of functional DnaseI was highly improved in *E. coli* cytoplasmic space by supplementation of cultivation medium with DTT during course of recombinant protein production.

EXAMPLE 9

DTT-mediated soluble accumulation and improved yield of active Sssl methyltransferase (from *Spiroplasma* sp).
Sssl Methyltransferase Contains 2 Cysteines.
Production Strain Preparation.

*E. coli* strain ER2566 was transformed with plasmid pACY184-TT-Sssl encoding Sssl methylase and plated on LB agar with chloramphenicol (35 μg $mL^{-1}$) for transformant selection. Transformation was based on the calcium temperature shock method.

Sssl Production in the Batch Shake Flasks.

The inoculums for batch protein production in the shake flasks were prepared by overnight batch cultivation of the selected clones in 500 mL shake flasks with 50 ml of LB medium. For protein production 5% of the corresponding inoculum culture was transferred to fresh LB medium to the final volume of 500 mL in 2 L baffled Erlenmeyer shake flasks. Cultures were cultivated at 37° C. and 180 rpm until they reached the induction point corresponding to cell density of $OD_{600}$=0.7±0.05 (μ≈0.5 $h^{-1}$). Induction was performed by addition of 1 M IPTG to the final concentration of 0.1 mM. DTT was added to the cultivation medium at the Sssl synthesis induction point as dry powder to achieve final concentration of 15 mM. Cytoplasmic expression was carried out for 4 h at 30° C. at the shaking rate of 180 rpm.

Protein Analysis

Cell samples harvested from flask or cultivations were resuspended in lysis buffer with the following biomass to buffer ratio: 1 g of biomass with 5 mL of lysis buffer (10 mM K-phosphate buffer pH 7.4, 10% glycerol, 200 mM NaCl, 1 mM EDTA, 1 mM DTT, 0.1% Tween-20 and 0.1 mg $mL^{-1}$ lysozyme). After 30 min of lysis at +4° C. the biomass was disrupted by sonication for 60 sec (Vibra cell™, Sonic and Materials Inc., 6 mm diameter probe tip) at 4° C. Soluble and insoluble protein fractions were separated by centrifugation for 30 min, 14000 rpm, 4° C. Total protein fraction is represented by cellular debris suspension (crude extract) before centrifugation. After centrifugation the insoluble protein pellet was additionally washed and resuspended in the original volume of lysis buffer without lysozyme.

For Sssl methyltransferase activity assay, crude cell extracts were diluted (5 times) with dilution buffer: 20 mM K-phosphate buffer (pH 7.4), 7 mM 2-mercaptoethanol, 0.2 mg/ml BSA, 1 mM $Na_2EDTA$, 200 mM KCl, 10% glycerol. The Sssl methyltransferase activity was evaluated by performing λ phage DNA methylation reaction in the mixture with the following components: 0.5, 1 2 and 3 μL of diluted crude extracts, 1 μg λ phage DNA, 50 μL Tango Buffer (Fermentas), 100 μM S-adenosylmethionine (SAM). The reaction was performed at 37° C. for 1 h. The reaction was stopped by 20 min heating at 65° C. After methylation reaction λ phage DNA was incubated with 1 μL (1 unit) of HpaII restriction enzyme (Fermentas, #ER0511), 30 min at 37° C. The reaction was stopped by heating at 65° C. for 10 minutes, afterwards mixture was supplemented with SDS containing loading dye (Fermentas #R1151) and $Na_2EDTA$ (final concentration of 5 mM). Fifteen μL of inactivated reaction mixture was applied on 1% agarose gel for DNA electrophoresis.

Samples for SDS-PAGE separation were prepared as follows: 20 μL of protein sample (total soluble, insoluble, protein suspensions), 25 μL of 4×SDS-PAGE loading buffer (Fermentas), 5 μL of 20×DTT (Fermentas) and 50 μL of deionized water to obtain a final sample volume of 100 μL. Samples were heated for 15 min at 95° C. Ten μL of sample was applied to each lane of a 10% SDS-PAGE gel.

Differences in the amounts of SssI in soluble protein fractions after test productions with and without DTT in the medium were evaluated from scanned SDS-PAGE gel images by image treatment with TotalLab software.

FIG. 19 shows an image of 1% agarose gel after DNA electrophoresis, with samples generated from soluble protein extracts incubation with 1 µg of Lamda phage DNA in SssI methyltransferase reaction mixture, followed by digestion with HpaII. Gel lane 1 "control"—λ phage DNA without methylation, after 30 min incubation with HpaII at 37° C. Gel lanes 2-5 represents samples from methylation/restriction reactions with 0.5, 1, 2 and 3 µL of crude extracts, generated after SssI synthesis without DTT in the cultivation medium. Gel lanes 6-10, represents samples from methylation/restriction reactions with 0.5, 1, 2 and 3 µL of crude extracts, generated after SssI synthesis with DTT in the cultivation medium.

FIGS. 20A-B show 10% SDS-PAGE images of normalized to equal amounts protein fractions, of *E. coli* pACY184-TT-SssI production construct after 4 hours of batch SssI production at 30° C. Panels are representing SDS-PAGE gel images with protein fractions after SssI production with no DTT in the medium (FIG. 20A) and with 15 mM DTT (FIG. 20B), respectively. Numbered lanes in the SDS-PAGE gels are representing: 1—soluble, 2—total and 3—insoluble protein fractions, 4 h after SssI synthesis induction. Arrow ◄ (FIGS. 20A-B) indicates SssI methyltransferase. Protein size marker: PageRuler™ Protein Ladder Plus (Fermentas). All cultures were initially started at 37° C., induced with 0.1 mM of IPTG. The SssI synthesis was performed at 30° C.

Conclusions from Example 9:
(i) Soluble accumulation of functional enzyme SssI (prokaryotic origin) in *E. coli* cytoplasmic space was improved by supplementation of the cultivation medium with DTT during the course of recombinant protein production.
(ii) Activity (folding) of functional SssI was highly improved in *E. coli* cytoplasmic space by supplementation of the cultivation medium with DTT during the course of recombinant protein production.

The references disclosed and cited below are expressly incorporated by reference herein in their entirety.

1. Baneyx F, Mujacic M. Recombinant protein folding and misfolding in *Escherichia coli*. Nat Biotechnol. 2004 November; 22(11):1399-408. Review.
2. Francis D M, Page R. Strategies to optimize protein expression in *E. coli*. Curr Protoc Protein Sci. 2010 August; Chapter 5:Unit 5.24.1-29. Review.
3. de Marco A. Strategies for successful recombinant expression of disulfide bond-dependent proteins in *Escherichia coli*. Microb Cell Fact. 2009 May 14; 8:26.
4. Wunderlich M, Glockshuber R.In vivo control of redox potential during protein folding catalyzed by bacterial protein disulfide-isomerase (DsbA). J Biol Chem. 1993 Nov. 25; 268(33):24547-50.
5. Walker K W, Gilbert H F: Effect of redox environment on the in vitro and in vivo folding of RTEM-1 beta-lactamase and *Escherichia coli* alkaline phosphatase. J Biol Chem 1994, 269: 28487-28493
6. Ostermeier M, De S K, Georgiou G: Eukaryotic protein disulfide isomerase complements *Escherichia coli* dsbA mutants and increases the yield of a heterologous secreted protein with disulfide bonds. J Biol Chem 1996, 271: 10616-10622.
7. Schäffner J, Winter J, Rudolph R, Schwarz E: Cosecretion of chaperones and low-molecular-size medium additives increases the yield of recombinant disulfide-bridged proteins. Appl Environ Microbiol 2001, 67: 3994-4000.
8. Gill R T, Cha H J, Jain A, Rao G, Bentley W E. Generating controlled reducing environments in aerobic recombinant *Escherichia coli* fermentations: effects on cell growth, oxygen uptake, heat shock protein expression, and in vivo CAT activity. Biotechnol Bioeng. 1998; 59:248-59.
9. Braakman I, Helenius J, Helenius A. Manipulating disulfide bond formation and protein folding in the endoplasmic reticulum. EMBO J. 1992 May; 11(5):1717-22.
10. Paunola E, Suntio T, Jämsä E, Makarow M. Folding of active beta-lactamase in the yeast cytoplasm before translocation into the endoplasmic reticulum. Mol Biol Cell. 1998. 4:817-27.
11. Jämsä E, Simonen M, Makarow M Selective retention of secretory proteins in the yeast endoplasmic reticulum by treatment of cells with a reducing agent. Yeast. 1994 March; 10(3):355-70.
12. Valetti C, Sitia R. The differential effects of dithiothreitol and 2-mercaptoethanol on the secretion of partially and completely assembled immunoglobulins suggest that thiol-mediated retention does not take place in or beyond the Golgi. Mol Biol Cell. 12:1311-24.
13. Mezghrani A, Fassio A, Benham A, Simmen T, Braakman I, Sitia R. Manipulation of oxidative protein folding and PDI redox state in mammalian cells. EMBO J. 22:6288-96
14. Kobe B, Kajava A V: The leucine-rich repeat as a protein recognition motif. Curr Opin Struct Biol 2001, 11:725-732.
15. Dickson K A, Haigis M C, Raines R T: Ribonuclease inhibitor: structure and function. Prog Nucleic Acid Res Mol Biol 2005, 80: 349-374.
16. Park H, Huxley-Jones J, Boot-Handford R P, Bishop P N, Attwood T K, Bella J: LRRCE: a leucine-rich repeat cysteinee capping motif unique to the chordate lineage. BMC Genomics 2008, 9: 599.
17. Fominaya J M, Hofsteenge J: Inactivation of ribonuclease inhibitor by thiol-disulfide exchange. J Biol Chem 1992, 267: 24655-24660.
18. Vicentini A M, Kieffer B, Matthies R, Meyhack B, Hemmings B A, Stone S R, Hofsteenge J: Protein chemical and kinetic characterization of recombinant porcine ribonuclease inhibitor expressed in Saccharomyces cerevisiae. Biochemistry 1990, 29: 8827-8834.
19. Lee F S, Vallee B L: Expression of human placental ribonuclease inhibitor in *Escherichia coli*. Biochem Biophys Res Commun 1989, 160: 115-120.
20. Klink T A, Vicentini A M, Hofsteenge J, Raines R T: High-level soluble production and characterization of porcine ribonuclease inhibitor. Protein Expr Purif 2001, 22:174-179.
21. Šiurkus J, Panula-Perälä J, Horn U, Kraft M, Rimseliene R, Neubauer P: Novel approach of high cell density recombinant bioprocess development: optimisation and scale-up from microliter to pilot scales while maintaining the fed-batch cultivation mode of *E. coli* cultures. Microb Cell Fact 2010, 9: 35.
22. Blackburn P, Wilson G, Moore S. Ribonuclease inhibitor from human placenta. Purification and properties. J Biol Chem. 1977 Aug. 25; 252(16):5904-10.
23. Blackburn P. Ribonuclease inhibitor from human placenta: rapid purification and assay. J Biol Chem. 1979 Dec. 25; 254(24):12484-7.
24. Kraft M, Knüpfer U, Wenderoth R, Kacholdt A, Pietschmann P, Hock B, Horn U: A dual expression platform to optimize the soluble production of heterologous proteins in the periplasm of *Escherichia coli*. Appl Microbiol Biotechnol 2007, 76: 1413-1422.

What is claimed is:

1. A method for producing from host cells an active heterologous polypeptide or protein comprising at least one disulfide bond, the method comprising
   (i) culturing host cells in a culture medium comprising a reducing agent having a reduction potential stronger than −0.1V at pH 7 and 25° C., to produce the heterologous polypeptide or protein with at least two cysteine residues in a reduced state, wherein a concentration of oxygen in the medium is less than 0.8%;
   (ii) recovering the heterologous polypeptide or protein from said host cells or from the culture medium; and
   (iii) exposing the heterologous polypeptide or protein to conditions which allow the at least two cysteine residues to form the at least one disulfide bonds; where the host cells comprise a nucleic acid encoding the heterologous protein or polypeptide, and where the reducing agent is capable of permeating the plasma membrane of the host cells.

2. The method of claim 1 where the host cells are prokaryotic cells.

3. The method of claim 2 where the prokaryotic cells are bacterial cells.

4. The method of claim 3 where the bacterial cells are *Escherichia coli* cells.

5. The method of claim 1 wherein step (iii) is conducted as part of step (ii) or step (iii) is conducted subsequently to step (ii).

6. The method of claim 1 where the heterologous polypeptide or protein is a deoxyribonuclease inhibitor.

7. The method of claim 1 wherein step (iii) comprises exposing the heterologous polypeptide or protein to calcium ions.

8. The method of claim 1 where the reducing agent is a thiol containing compound.

9. The method of claim 8 where the reducing agent comprises at least two thiol groups.

10. The method of claim 1 where the reducing agent has a reduction potential stronger than −0.2V at pH 7 and 25° C.

11. The method of claim 1 where the reducing agent is dithiothreitol or dithioerythritol.

12. The method of claim 11 where the reducing agent is present in the culture medium at a concentration of 2 mM to 18 mM.

13. The method of claim 1 where the heterologous polypeptide or protein is recovered from the cytoplasm of the host cells.

14. The method of claim 1 where the host cell is a prokaryotic cell and the heterologous polypeptide or protein is recovered from the periplasm of the prokaryotic cell.

15. The method of claim 1 where step (i) is conducted at a temperature below 37° C.

16. The method of claim 15 where the temperature is between 15° C. and 30° C.

17. The method of claim 1 where the nucleic acid encoding the heterologous protein or polypeptide is expressed under the control of a pCU promoter, and/or comprises -var or -lac ribosome binding sites.

18. The method of claim 1 wherein the host cells further express molecular chaperones.

19. The method of claim 18 where the molecular chaperones are GroEL and GroES.

* * * * *